(12) United States Patent
Lang

(10) Patent No.: US 7,717,956 B2
(45) Date of Patent: May 18, 2010

(54) JOINT ARTHROPLASTY DEVICES FORMED IN SITU

(75) Inventor: Philipp Lang, Lexington, MA (US)

(73) Assignee: ConforMIS, Inc., Burlington, MA (US)

(*) Notice: Subject to any disclaimer, the term of this patent is extended or adjusted under 35 U.S.C. 154(b) by 42 days.

(21) Appl. No.: 11/326,705

(22) Filed: Nov. 22, 2005

(65) Prior Publication Data

US 2007/0250169 A1 Oct. 25, 2007

Related U.S. Application Data

(63) Continuation-in-part of application No. 10/724,010, filed on Nov. 25, 2003, which is a continuation-in-part of application No. 10/305,652, filed on Nov. 27, 2002, which is a continuation-in-part of application No. 10/160,667, filed on May 28, 2002.

(60) Provisional application No. 60/630,516, filed on Nov. 23, 2004, provisional application No. 60/293,488, filed on May 25, 2001, provisional application No. 60/363,527, filed on Mar. 12, 2002, provisional application No. 60/380,695, filed on May 14, 2002, provisional application No. 60/380,692, filed on May 14, 2002.

(51) Int. Cl.
*A61F 2/44* (2006.01)

(52) U.S. Cl. ............ 623/14.12; 623/17.12; 623/18.11

(58) Field of Classification Search .......... 623/14.12, 623/17.11–17.16, 16.11, 18.11; 606/61, 606/90

See application file for complete search history.

(56) References Cited

U.S. PATENT DOCUMENTS

| 3,798,679 A | 3/1974 | Ewald | 3/1 |
| 4,052,753 A | 10/1977 | Dedo | 3/1 |
| 4,055,862 A | 11/1977 | Farling | 3/1.91 |
| 4,085,466 A | 4/1978 | Goodfellow et al. | 3/1.91 |
| 4,203,444 A | 5/1980 | Bonnell et al. | 128/176 |
| 4,340,978 A | 7/1982 | Buechel et al. | 3/1.911 |
| 4,436,684 A | 3/1984 | White | 264/138 |
| 4,502,161 A | 3/1985 | Wall | 3/1.91 |
| 4,586,496 A | 5/1986 | Keller | 128/92 |
| 4,601,290 A | 7/1986 | Effron et al. | 128/305 |
| 4,609,551 A | 9/1986 | Caplan et al. | 424/95 |

(Continued)

FOREIGN PATENT DOCUMENTS

DE 3516743 11/1986

(Continued)

OTHER PUBLICATIONS

Taha et al., "Modeling and design of a custom made cranium implant for large skull reconstruction before a tumor removal", Phidias Newsletter No. 6, pp. 3, 6, Jun. 2001. Retrieved from the Internet: URL: http://www.materialise.com/medical/files/pdf.

(Continued)

*Primary Examiner*—Pedro Philogene
(74) *Attorney, Agent, or Firm*—Sunstein Kann Murphy & Timbers LLP

(57) ABSTRACT

Disclosed herein are methods and devices for repairing articular surfaces. The articular surface repairs are customizable or highly selectable by patient and geared toward providing optimal fit and function.

41 Claims, 10 Drawing Sheets

U.S. PATENT DOCUMENTS

| | | | |
|---|---|---|---|
| 4,627,853 A | 12/1986 | Campbell et al. | 623/16 |
| 4,769,040 A | 9/1988 | Wevers | 623/20 |
| 4,846,835 A | 7/1989 | Grande | 623/11 |
| 4,865,607 A | 9/1989 | Witzel et al. | 623/20 |
| 4,880,429 A | 11/1989 | Stone | 623/18 |
| 5,041,138 A | 8/1991 | Vacanti et al. | 623/16 |
| 5,059,216 A | 10/1991 | Winters | 623/20 |
| 5,067,964 A | 11/1991 | Richmond et al. | 623/18 |
| 5,129,908 A | 7/1992 | Petersen | 606/88 |
| 5,133,759 A | 7/1992 | Turner | 623/20 |
| 5,154,717 A | 10/1992 | Matsen, III et al. | 606/53 |
| 5,171,322 A | 12/1992 | Kenny | 623/18 |
| 5,197,985 A | 3/1993 | Caplan et al. | 623/549 |
| 5,206,023 A | 4/1993 | Hunziker | 424/423 |
| 5,226,914 A | 7/1993 | Caplan et al. | 623/549 |
| 5,270,300 A | 12/1993 | Hunziker | 514/12 |
| 5,306,311 A | 4/1994 | Stone et al. | 623/18 |
| 5,314,482 A | 5/1994 | Goodfellow et al. | 623/20 |
| 5,344,459 A * | 9/1994 | Swartz | 623/14.12 |
| 5,368,858 A | 11/1994 | Hunziker | 424/423 |
| 5,468,787 A | 11/1995 | Braden et al. | 523/113 |
| 5,480,430 A * | 1/1996 | Carlisle et al. | 623/8 |
| 5,501,687 A | 3/1996 | Willert et al. | 606/94 |
| 5,503,162 A | 4/1996 | Athanasiou et al. | 128/774 |
| 5,556,432 A | 9/1996 | Kubein-Messenburg et al. | 623/20 |
| 5,632,745 A | 5/1997 | Schwartz | 606/75 |
| 5,671,741 A | 9/1997 | Lang et al. | 128/653 |
| 5,682,886 A | 11/1997 | Delp et al. | 128/653.1 |
| 5,683,466 A | 11/1997 | Vitale | 623/18 |
| 5,728,162 A | 3/1998 | Eckhoff | 623/20 |
| 5,749,874 A | 5/1998 | Schwartz | 606/75 |
| 5,749,876 A | 5/1998 | Duvillier et al. | 606/88 |
| 5,769,899 A | 6/1998 | Schwartz et al. | 623/18 |
| 5,786,217 A | 7/1998 | Tubo et al. | 435/402 |
| 5,827,289 A | 10/1998 | Reiley et al. | 606/86 |
| 5,835,619 A | 11/1998 | Morimoto et al. | 382/132 |
| 5,840,443 A | 11/1998 | Gregg et al. | 429/212 |
| 5,842,477 A | 12/1998 | Naughton et al. | 128/898 |
| 5,853,746 A | 12/1998 | Hunziker | 424/426 |
| 5,871,018 A | 2/1999 | Delp et al. | 128/898 |
| 5,871,542 A | 2/1999 | Goodfellow et al. | 623/20 |
| 5,871,546 A | 2/1999 | Colleran et al. | 623/20 |
| 5,879,390 A | 3/1999 | Kubein-Meesenburg et al. | 623/20 |
| 5,885,296 A | 3/1999 | Masini | 606/86 |
| 5,885,298 A | 3/1999 | Herrington et al. | 606/88 |
| 5,888,220 A * | 3/1999 | Felt et al. | 128/898 |
| 5,897,559 A | 4/1999 | Masini | 606/86 |
| 5,900,245 A | 5/1999 | Sawhney et al. | 424/426 |
| 5,906,934 A | 5/1999 | Grande et al. | 435/325 |
| 5,916,220 A | 6/1999 | Masini | 606/88 |
| 5,939,323 A | 8/1999 | Valentini et al. | 435/395 |
| 5,961,523 A | 10/1999 | Masini | 606/86 |
| 5,968,051 A | 10/1999 | Luckman et al. | 606/88 |
| 5,972,385 A | 10/1999 | Liu et al. | 424/486 |
| 6,046,379 A | 4/2000 | Stone et al. | 623/11 |
| 6,082,364 A | 7/2000 | Balian et al. | 128/898 |
| 6,090,144 A | 7/2000 | Letot et al. | 623/20 |
| 6,093,204 A | 7/2000 | Stone | 623/14.12 |
| 6,102,916 A | 8/2000 | Masini | 606/88 |
| 6,110,209 A | 8/2000 | Stone | 623/16.11 |
| 6,120,541 A | 9/2000 | Johnson | 623/14.12 |
| 6,126,690 A | 10/2000 | Ateshian et al. | 623/18 |
| 6,132,468 A * | 10/2000 | Mansmann | 623/20.16 |
| 6,139,578 A | 10/2000 | Lee et al. | 623/16.11 |
| 6,156,069 A | 12/2000 | Amstutz | 623/22.11 |
| 6,187,010 B1 | 2/2001 | Masini | 606/86 |
| 6,200,606 B1 | 3/2001 | Peterson et al. | 424/574 |
| 6,203,576 B1 | 3/2001 | Afriat et al. | 623/20.27 |
| 6,206,927 B1 | 3/2001 | Fell et al. | 623/20.29 |
| 6,214,369 B1 | 4/2001 | Grande et al. | 424/423 |
| 6,217,894 B1 | 4/2001 | Sawhney et al. | 424/426 |
| 6,219,571 B1 | 4/2001 | Hargreaves et al. | 600/410 |
| 6,228,116 B1 * | 5/2001 | Ledergerber | 623/8 |
| 6,248,110 B1 * | 6/2001 | Reiley et al. | 606/93 |
| 6,251,143 B1 | 6/2001 | Schwartz et al. | 623/23.72 |
| 6,277,151 B1 | 8/2001 | Lee et al. | 623/23.61 |
| 6,281,195 B1 | 8/2001 | Rueger et al. | 514/21 |
| 6,283,980 B1 | 9/2001 | Vibe-Hansen et al. | 606/151 |
| 6,299,905 B1 | 10/2001 | Peterson et al. | 424/486 |
| 6,328,765 B1 | 12/2001 | Hardwick et al. | 623/23.72 |
| 6,344,043 B1 | 2/2002 | Pappas | 606/96 |
| 6,344,059 B1 | 2/2002 | Krakovits et al. | 623/20.21 |
| 6,352,558 B1 | 3/2002 | Spector | 623/18.11 |
| 6,358,253 B1 | 3/2002 | Torrie et al. | 606/96 |
| 6,371,958 B1 | 4/2002 | Overaker | 606/72 |
| 6,375,658 B1 | 4/2002 | Hangody et al. | 623/20.18 |
| 6,379,367 B1 | 4/2002 | Vibe-Hansen et al. | 606/151 |
| 6,383,228 B1 | 5/2002 | Schmotzer | 623/23.35 |
| 6,429,013 B1 | 8/2002 | Halvorsen et al. | 435/377 |
| 6,443,988 B2 * | 9/2002 | Felt et al. | 623/17.12 |
| 6,444,222 B1 | 9/2002 | Asculai et al. | 424/484 |
| 6,459,948 B1 | 10/2002 | Ateshian et al. | 700/117 |
| 6,468,314 B2 | 10/2002 | Schwartz et al. | 623/23.72 |
| 6,479,996 B1 | 11/2002 | Hoogeveen et al. | 324/309 |
| 6,520,964 B2 | 2/2003 | Tallarida et al. | 606/71 |
| 6,558,421 B1 | 5/2003 | Fell et al. | 623/14.12 |
| 6,626,945 B2 | 9/2003 | Simon et al. | 623/17.19 |
| 6,632,235 B2 * | 10/2003 | Weikel et al. | 606/192 |
| 6,652,587 B2 | 11/2003 | Felt et al. | 623/20.16 |
| 6,679,917 B2 | 1/2004 | Ek | 600/587 |
| 6,916,341 B2 | 7/2005 | Rolston | 623/20.3 |
| 7,044,954 B2 * | 5/2006 | Reiley et al. | 606/93 |
| 2001/0001120 A1 | 5/2001 | Masini | 606/86 |
| 2001/0010023 A1 | 7/2001 | Schwartz et al. | 623/23.72 |
| 2001/0039455 A1 | 11/2001 | Simon et al. | 623/23.51 |
| 2002/0013626 A1 | 1/2002 | Geistlich et al. | 623/23.57 |
| 2002/0045940 A1 | 4/2002 | Giannetti et al. | 623/11.11 |
| 2002/0059049 A1 | 5/2002 | Bradbury et al. | 703/11 |
| 2002/0068979 A1 | 6/2002 | Brown et al. | 623/20.3 |
| 2002/0082703 A1 | 6/2002 | Repicci | 623/20.29 |
| 2002/0087274 A1 | 7/2002 | Alexander et al. | 702/19 |
| 2002/0106625 A1 | 8/2002 | Hung et al. | 435/1.1 |
| 2002/0115647 A1 | 8/2002 | Halvorsen et al. | 514/171 |
| 2002/0120274 A1 | 8/2002 | Overaker et al. | 606/72 |
| 2002/0120281 A1 | 8/2002 | Overaker | 606/151 |
| 2002/0127264 A1 | 9/2002 | Felt et al. | 424/423 |
| 2002/0133230 A1 | 9/2002 | Repicci | 623/14.12 |
| 2002/0151986 A1 | 10/2002 | Asculai et al. | 424/484 |
| 2002/0173852 A1 | 11/2002 | Felt et al. | 623/20.32 |
| 2002/0183850 A1 | 12/2002 | Felt et al. | 623/20.16 |
| 2003/0055500 A1 | 3/2003 | Fell et al. | 623/14.12 |
| 2003/0055501 A1 | 3/2003 | Fell et al. | 623/14.12 |
| 2003/0055502 A1 | 3/2003 | Lang et al. | 623/16.11 |
| 2003/0060882 A1 | 3/2003 | Fell et al. | 623/14.12 |
| 2003/0060883 A1 | 3/2003 | Fell et al. | 623/14.12 |
| 2003/0060884 A1 | 3/2003 | Fell et al. | 623/14.12 |
| 2003/0060885 A1 | 3/2003 | Fell et al. | 623/14.12 |
| 2003/0100953 A1 | 5/2003 | Rosa et al. | 623/20.3 |
| 2003/0158606 A1 | 8/2003 | Coon et al. | 623/20.15 |
| 2003/0216669 A1 | 11/2003 | Lang et al. | 600/587 |
| 2003/0225457 A1 | 12/2003 | Justin et al. | 623/20.14 |
| 2004/0102852 A1 | 5/2004 | Johnson et al. | 623/20.15 |
| 2004/0122521 A1 | 6/2004 | Lee et al. | 623/20.15 |
| 2004/0133276 A1 | 7/2004 | Lang et al. | 623/14.12 |
| 2004/0138754 A1 | 7/2004 | Lang et al. | 623/20.14 |
| 2004/0147927 A1 | 7/2004 | Tsougarakis et al. | 606/53 |
| 2004/0153079 A1 | 8/2004 | Tsougarakis et al. | 606/77 |
| 2004/0153162 A1 | 8/2004 | Sanford et al. | 623/20.3 |
| 2004/0153164 A1 | 8/2004 | Sanford et al. | 623/20.29 |
| 2004/0167390 A1 | 8/2004 | Alexander et al. | 600/410 |
| 2004/0167630 A1 | 8/2004 | Rolston | 623/20.14 |
| 2004/0193280 A1 | 9/2004 | Webster et al. | 623/20.33 |

| | | | | | | |
|---|---|---|---|---|---|---|
| 2004/0204644 | A1 | 10/2004 | Tsougarakis et al. ......... 600/410 | WO | WO 02/34310 | 5/2002 |
| 2004/0204760 | A1 | 10/2004 | Fitz et al. ................. 623/14.12 | WO | WO 02/36147 | 5/2002 |
| 2004/0236424 | A1 | 11/2004 | Berez et al. .............. 623/14.12 | WO | WO 02/096268 | 12/2002 |
| 2005/0015153 | A1 | 1/2005 | Goble et al. ............. 623/23.46 | WO | WO 03/007788 | 1/2003 |
| 2005/0043807 | A1 | 2/2005 | Wood ...................... 623/20.14 | WO | WO 03/047470 | 6/2003 |
| 2005/0085920 | A1 | 4/2005 | Williamson .............. 623/20.14 | WO | WO 03/051210 | 6/2003 |
| 2005/0107883 | A1 | 5/2005 | Goodfried et al. ........ 623/20.15 | WO | WO 2004/043305 | 5/2004 |
| 2005/0107884 | A1 | 5/2005 | Johnson et al. .......... 623/20.15 | WO | WO 2005/051239 | 6/2005 |
| 2005/0171612 | A1 | 8/2005 | Rolston .................... 623/20.19 | | | |
| 2005/0234461 | A1 | 10/2005 | Burdulis, Jr. et al. ........... 606/79 | | | |
| 2005/0267584 | A1 | 12/2005 | Burdulis, Jr. et al. ..... 623/20.19 | | | |
| 2006/0111722 | A1 | 5/2006 | Bouadi ........................ 606/79 | | | |
| 2007/0198022 | A1 | 8/2007 | Lang et al. ................... 606/88 | | | |

FOREIGN PATENT DOCUMENTS

| | | |
|---|---|---|
| EP | 0528080 | 8/1991 |
| EP | 0626156 | 1/1992 |
| EP | 0530804 | 9/1992 |
| EP | 0613380 | 11/1992 |
| EP | 0814731 | 1/1996 |
| EP | 0732091 | 3/1996 |
| EP | 0833620 | 6/1996 |
| EP | 0896825 | 8/1997 |
| EP | 0809987 | 12/1997 |
| EP | 1077253 | 8/2000 |
| EP | 1120087 | 1/2001 |
| EP | 1129675 | 3/2001 |
| EP | 1132061 | 9/2001 |
| EP | 1234552 | 2/2002 |
| EP | 1234555 | 2/2002 |
| FR | 2819714 | 7/2002 |
| GB | 2291355 | 1/1996 |
| GB | 2348373 | 10/2000 |
| JP | 1-249049 | 3/1988 |
| JP | 8-173465 | 12/1994 |
| JP | 9-206322 | 2/1996 |
| WO | WO 90/09769 | 9/1990 |
| WO | WO 93/04710 | 3/1993 |
| WO | WO 93/09819 | 5/1993 |
| WO | WO 93/25157 | 12/1993 |
| WO | WO 95/27450 | 10/1995 |
| WO | WO 95/28688 | 10/1995 |
| WO | WO 95/30390 | 11/1995 |
| WO | WO 95/32623 | 12/1995 |
| WO | WO 96/24302 | 8/1996 |
| WO | WO 97/25942 | 7/1997 |
| WO | WO 97/26847 | 7/1997 |
| WO | WO 97/38676 | 10/1997 |
| WO | WO 98/12994 | 4/1998 |
| WO | WO 98/30617 | 7/1998 |
| WO | WO 99/02654 | 1/1999 |
| WO | WO 99/08728 | 2/1999 |
| WO | WO 99/42061 | 8/1999 |
| WO | WO 99/47186 | 9/1999 |
| WO | WO 99/51719 | 10/1999 |
| WO | WO 99/56674 | 11/1999 |
| WO | WO 00/09179 | 2/2000 |
| WO | WO 00/35346 | 6/2000 |
| WO | WO 00/48550 | 8/2000 |
| WO | WO 00/59411 | 10/2000 |
| WO | WO 00/74554 | 12/2000 |
| WO | WO 01/10356 | 2/2001 |
| WO | WO 01/17463 | 3/2001 |
| WO | WO 01/19254 | 3/2001 |
| WO | WO 01/35968 | 5/2001 |
| WO | WO 01/45764 | 6/2001 |
| WO | WO 01/68800 | 9/2001 |
| WO | WO 01/70142 | 9/2001 |
| WO | WO 01/91672 | 12/2001 |
| WO | WO 02/22013 | 3/2002 |
| WO | WO 02/22014 | 3/2002 |
| WO | WO 02/23483 | 3/2002 |

OTHER PUBLICATIONS

Kidder J. et al., "3D model acquisition, design, planning and manufacturing of orthopaedic devices: a framework", Proceedings of theSPIE—Advanced Sensor and Control-Sustem Interface, Boston, MA, vol. 2911, pp. 9-22, Nov. 21, 1996.

Carr J.C. et al., "Surface Interpolation with Radial Basis Functions for Medical Imaging", IEEE Transactions on Medical Imaging, IEEE, Inc. New York, vol. 16, No. 1, Feb. 1, 1997, pp. 96-107.

C.S. Ranawat et al., "MacIntosh Hemiarthroplasty in Rheumatoid Knee" Acta Orthop Belg. Jan.-Feb. 1973: 39(1):102-112.

B. Blum et al., "Knee Arthroplasty in Patients with Rheumatoid Arthritis", Ann. Rheum. Dis. Jan. 1974: 33(1):1-11.

Nelson M.D. et al., "Arthroplasty and Arthrodesis of the Knee Joint", Orthop. Clin. North Am. Mar. 1971: 2(1):245-64.

McCollum et al., "Tibial Plateau Prosthesis in Arthroplasty of the Knee", J. Bone Joint Surg. Am. Jun. 1970:52(4):827-8.

Hastings D.E. et al., "Double Hemiarthroplasty of the Knee in Rheumatoid Arthritis. A Survey of Fifty Consecutive Cases", J. Bone Joint Surg. Br. Feb. 1973:55(1):112-118.

Schron, D. et al., "MacIntosh Arthroplasty in Rheumatoid Arthritis", Rheumatol Rehabil. Aug. 1978:17(3):155-163.

McKeever, D.C. et al., "The Classic Tibial Plateau Prosthesis", Clin. Orthop. Relat. Res. Jan.-Feb. 1985:(192):3-12.

Conaty et al., "Surgery of the Hip and Knee in Patients with Rheumatoid Arthritis", J. Bone Joint Surg. Am. Mar. 1973:55(2):301-314.

MacIntosh et al., "The Use of the Hemiarthroplasty Prosthesis for Advanced Osteoarthritis and Rheumatoid Arthritis of the Knee", J. of Bone & Joint Surg. 1972, vol. 54B, No. 2, pp. 244-255.

MacIntosh, "Arthroplasty of the Knee in Rheumatoid Arthritis Using the Hemiarthroplasty Prosthesis", Synovectomy and Arthroplasty in Rheumatoid Arthritis pp. 79-80, Second Int'l. Symposium, Jan. 27-29, 1967 (Basle, Switzerland).

MacIntosh, D.L., "Hemiarthroplasty of the Knee Using a Space Occupying Prosthesis for Painful Varus and Valgus Deformities", J. Bone Joint Surg. Am. Dec. 1958:40-A:1431.

Stauffer R. et al., "The MacIntosh Prosthesis. Prospective Clinical and Gait Evaluation", Arch. Surg. Jun. 1975:110(6):717-720.

Clary BB et al., "Experience with the MacIntosh Knee Prosthesis", South Med. J. Mar. 1972:65(3):265-272.

Ghelman MD, et al., "Kinematics of the Knee After Prosthetic Replacements", Clin. Orthop. May 1975: (108): 149-157.

Henderson, MD et al., "Experience with the Use of the Macintosh Prosthesis in Knees of Patients with Rheumatoid Arthritis", South. Med. J. Nov. 1969:62(11):1311-1315.

Potter M.D., "Arthroplasty of the Knee With Tibial Metallic Implants of the McKeever and MacIntosh Design", Sug. Clin. North Am. Aug. 1969:49(4):903-915.

Potter T.A., et al., "Arthroplasty of the Knee in Rheumatoid Arthritis and Osteoarthritis: A Follow-up Study After Implantation of the McKeever and MacIntosh Prostheses", J. Bone Joint Surg. Am. Jan. 1972:54(1):1-24.

Bogoch et al., "Supracondylar Fractures of the Femur Adjacent to Resurfacing and MacIntosh Arthroplasties of the Knee in Patients with Rheumatoid Arthritis", Clin. Orthop. Apr. 1988(229):213-220.

Cameron et al., "Review of a Failed Knee Replacement and Some Observations on the Design of a Knee Resurfacing Prosthesis", Arch. Orthop Trauma Surg. 1980:97(2):87-89.

Kates A. et al., "Experiences of Arthroplasty of the Rheumatoid Knee Using MacIntosh Prostheses", Ann. Rheum. Dis. May 1969:28(3):328.

Jessop J.D. et al., "Follow-up of the MacIntosh Arthroplasty of the Knee Joint", Rheumatol Phys. Med. Feb. 1972: 11 (5): 217-224.

Andersson GB et al., "MacIntosh Arthroplasty In Rheumatoid Arthrisit", Acta. Orthrop. Scand. 1974:45 (2): 245-259.

Wordsworth et al., "MacIntosh Arthroplasty for the Rheumatoid Knee: A 10-year Follow Up", Ann. Rheum. Dis. Nov. 1985:44 (11): 738-741.

Kay N.R. et al., "MacIntosh Tibial Plateau Hemiprosthesis for the Rheumatoid Knee", J. Bone Joint Sur. Br. May 1972: 54(2): 256-262.

Porter M.L. et al., "MacIntosh Arthroplasty: a long-term review", J. R. Coll. Sur. Edinb. Jan.-Feb. 1988: (192): 199-201.

Vande Berg et al., "Assessment of Knee Cartilage in Cadavers with Dual-Detector Spiral CT Arthrography and MR Imaging", published online before print 10.1148/radiol.2222010597, Radiology 2002; 22: pp. 430-436.

MacIntosh, "Arthroplasty of the Knee in Rheumatoid Arthritis", Proceedings and Reports of councils and Associations, J. Bone & Joint Surg. (Feb. 1966), vol. 48B No. (1): 179.

Leenslag et al., "A Porous Composite for Reconstruction of Meniscus Lesions", Biological and Biomechanical Performance of Biomaterials, Elsevier Science Publishers B.V., Amsterdam, 1986, pp. 147-152.

Platt et al., "Mould Arthroplasty of the Knee: A Ten-Year Follow-up Study", Oxford Regional Rheumatic Diseases Research Centre, J. of Bone and Joint Surg., vol. 51B, No. 1, Feb. 1969, pp. 76-87.

Stout et al., X-ray Structure Determination, a Practical Guide, Copyright 1968, Table of Contents.

Slone et al., Body CT, A Practical Approach, Copyright 2000, ISBN 0-07-058219-X, Table of Contents.

Lam et al., X-Ray Diagnosis: A Physician's Approach, ISBN 981-2083, 24-7, Index.

Tamez-Pena et al., MRI Isotropic Resolution Reconstruction from two Orthogonal Scans, Medical Imaging 2001: vol. 4322, pp. 87-97.

Brown, Ph.D. et al., MRI Basic Principals and Applications, $2^{nd}$ Edition, A. John Wiley & Sons, Inc., 1955, Table of Contents.

Argenson et al., "Is There a Place for Patellofemoral Arthroplasty?", Clinical Orthopaedics and Related Research No. 321, pp. 162-167, 1995.

DeWinter et al., "The Richards type 11 patellofemoral arthroplasty", Acta Orthop Scand 2001; 72 (5); 487-490.

Radermacher, Klaus, Helmholtz Institute of Biomedical Technology, "Computer-Assisted Planning and Execution of Orthopedic Surgery Using Individual Surgical Templates", May 18, 1999.

Radermacher, Klaus, German version: Helmholtz Institute of Biomedical Technology, "Computer-Assisted Planning and Execution of Orthopedic Surgery Using Individual Surgical Templates", May 18, 1999.

Radermacher, Klaus, "Computer Assisted Orthopaedic Surgery With Image Based Individual Templates" *Clinical Orthopaedics*, Sep. 1998, vol. 354, pp. 28-38.

Portheine, F., Radermacher K., Zimolong, A., et al, "Development of a Clinical Demonstrator for Computer Assisted Orthopedic Surgery with CT Image Based Individual Templates." In Lemke HU, Vannier MW, Inamura K (eds). *Computer Assisted Radiology and Surgery*. Amsterdam, Elsevier 944-949, 1997.

Radermacher, K., Protheine, F., Zimolong, A., et al, "Image Guided Orthopedic Surgery Using Individual Templates—Experimental Results and Aspects of the Development of a Demonstrator for Pelvis Surgery." In Troccaz J. Grimson E., Mosges R (eds). *Computer Vision, Virtual Reality and Robotics in Medicine and Medical Robotics and Computer Assisted Surgery, Lecture Notes in Computer Science*. Berlin, Springer-Verlag 606-616, 1997.

Radermacher, K., Rau, G., Staudte HW, "Computer Integrated Orthopedic Surgery—Connection of Planning and Execution in Surgical Inventions." In Taylor, R., Lavallee, S., Burdea G. Mosges, R. (eds). *Computer Integrated Surgery*. Cambridge, MIT press 451-463, 1996.

Radermacher, K., Staudte HW, Rau, G., "Technique for Better Execution of CT Scan Planned Orthopedic Surgery on Bone Structures." In Lemke HW, Inamura, K., Jaffe, CC, Vannier, MW (eds). *Computer Assisted Radiology*, Berlin, Springer 933-938, 1995.

Radermacher, K., Staudte, HW, Rau, G., "CT Image Based Planning and Execution of Interventions in Orthopedic Surgery Using Individual Templates—Experimental Results and A spects of Clinical Applications." In Nolte LP, Ganz, R. (eds). CAOS—*Computer Assisted Orthopaedic Surgery*. Bern, Hans Huber (In Press) 1998.

International Searching Authority, International Search Report—International Application No. PCT/US03/32123, dated Mar. 17, 2004, 9 pages.

International Searching Authority, International Search Report—International Application No. PCT/US04/39616, dated Mar. 28, 2005, 7 pages.

International Searching Authority, International Search Report—International Application No. PCT/US04/039616, dated Feb. 23, 2005, 10 pages.

International Searching Authority, International Search Report—International Application No. PCT/US04/39714, dated May 13, 2005, together with Written Opinion of the International Searching Authority, 8 pages.

European Patent Office, European Search Report—Application No. EP 03 79 0194, dated Jul. 6, 2006, 5 pages.

International Searching Authority, International Search Report—International Application No. PCT/US2006/045172, together with Written Opinion of the International Searching Authority, dated Apr. 19, 2007, 14 pages.

International Searching Authority, International Search Report—International Application No. PCT/US2005/044008, dated Mar. 30, 2006, 3 pages.

International Bureau, International Preliminary Report on Patentability—International Application No. PCT/US2005/044008, dated Jun. 5, 2007, together with Written Opinion of the International Searching Authority, 8 pages.

International Searching Authority, International Search Report—International Application No. PCT/US2007/016181, together with Written Opinion of the International Searching Authority, mailed Sep. 7, 2007, received Sep. 10, 2007, 15 pages.

European Patent Office, Supplementary European Search Report—Application No. 04812187.5-2310, PCT/US2004/039616, dated Sep. 19, 2007, received Oct. 10, 2007, 3 pages.

* cited by examiner

FIG. 11E  FIG. 11F

JOINT ARTHROPLASTY DEVICES FORMED IN SITU

CROSS-REFERENCE TO RELATED APPLICATIONS

This is a continuation of U.S. Ser. No. 60/630,516 entitled "Joint Arthroplasty Devices Formed in Situ" filed Nov. 23, 2004 and a continuation-in-part of U.S. Ser. No. 10/724,010 entitled "METHODS AND COMPOSITIONS FOR ARTICULAR REPAIR" filed Nov. 25, 2003 which is a continuation-in-part of U.S. Ser. No. 10/305,652 entitled "METHODS AND COMPOSITIONS FOR ARTICULAR REPAIR," filed Nov. 27, 2002, which is a continuation-in-part of U.S. Ser. No. 10/160,667, filed May 28, 2002, which in turn claims the benefit of U.S. Ser. No. 60/293,488 entitled "METHODS TO IMPROVE CARTILAGE REPAIR SYSTEMS", filed May 25, 2001, U.S. Ser. No. 60/363,527, entitled "NOVEL DEVICES FOR CARTILAGE REPAIR," filed Mar. 12, 2002 and U.S. Ser. Nos. 60/380,695 and 60/380,692, entitled "METHODS AND COMPOSITIONS FOR CARTILAGE REPAIR," and "METHODS FOR JOINT REPAIR," filed May 14, 2002, all of which applications are hereby incorporated by reference in its entirety.

FIELD OF THE INVENTION

The present invention relates to orthopedic methods, systems and prosthetic devices and more particularly relates to methods, systems and devices for articular surface repair in the spine and in the extremities.

BACKGROUND OF THE INVENTION

Adult cartilage has a limited ability of repair; thus, damage to cartilage produced by disease, such as rheumatoid and/or osteoarthritis, or trauma can lead to serious physical deformity and debilitation. Furthermore, as human articular cartilage ages, its tensile properties change. The superficial zone of the knee articular cartilage exhibits an increase in tensile strength up to the third decade of life, after which it decreases markedly with age as detectable damage to type II collagen occurs at the articular surface. The deep zone cartilage also exhibits a progressive decrease in tensile strength with increasing age, although collagen content does not appear to decrease. These observations indicate that there are changes in mechanical and, hence, structural organization of cartilage with aging that, if sufficiently developed, can predispose cartilage to traumatic damage.

For example, the superficial zone of the knee articular cartilage exhibits an increase in tensile strength up to the third decade of life, after which it decreases markedly with age as detectable damage to type II collagen occurs at the articular surface. The deep zone cartilage also exhibits a progressive decrease in tensile strength with increasing age, although collagen content does not appear to decrease. These observations indicate that there are changes in mechanical and, hence, structural organization of cartilage with aging that, if sufficiently developed, can predispose cartilage to traumatic damage.

Once damage occurs, joint repair can be addressed through a number of approaches. One approach includes the use of matrices, tissue scaffolds or other carriers implanted with cells (e.g., chondrocytes, chondrocyte progenitors, stromal cells, mesenchymal stem cells, etc.). These solutions have been described as a potential treatment for cartilage and meniscal repair or replacement. See, also, International Publications WO 99/51719 to Fofonoff, published Oct. 14, 1999; WO01/91672 to Simon et al., published Dec. 6, 2001; and WO01/17463 to Mannsmann, published Mar. 15, 2001. However, clinical outcomes with biologic replacement materials such as allograft and autograft systems and tissue scaffolds have been uncertain since most of these materials cannot achieve a morphologic arrangement or structure similar to or identical to that of normal, disease-free human tissue it is intended to replace. Moreover, the mechanical durability of these biologic replacement materials remains uncertain.

Usually, severe damage or loss of cartilage is treated by replacement of the joint with a prosthetic material, for example, silicone, e.g. for cosmetic repairs, or metal alloys. See, e.g., U.S. Pat. No. 6,383,228 to Schmotzer, issued May 7, 2002. Implantation of prosthetic devices is usually associated with loss of underlying tissue and bone without recovery of the full function allowed by the original cartilage and, with some devices, serious long-term complications associated with the loss of significant amount of tissue and bone can include infection, osteolysis and also loosening of the implant.

Further, joint arthroplasties are highly invasive and require surgical resection of the entire or the majority of the articular surface of one or more bones. With these procedures, the marrow space is reamed in order to fit the stem of the prosthesis. The reaming results in a loss of the patient's bone stock. U.S. Pat. No. 5,593,450 to Scott et al. issued Jan. 14, 1997 discloses an oval domed shaped patella prosthesis. The prosthesis has a femoral component that includes two condyles as articulating surfaces. The two condyles meet to form a second trochlear groove and ride on a tibial component that articulates with respect to the femoral component. A patella component is provided to engage the trochlear groove. U.S. Pat. No. 6,090,144 to Letot et al. issued Jul. 18, 2000 discloses a knee prosthesis that includes a tibial component and a meniscal component that is adapted to be engaged with the tibial component through an asymmetrical engagement.

A variety of materials can be used in replacing a joint with a prosthetic, for example, silicone, e.g. for cosmetic repairs, or suitable metal alloys are appropriate. See, e.g., U.S. Pat. No. 6,443,991 B1 to Running issued Sep. 3, 2002. Implantation of these prosthetic devices is usually associated with loss of underlying tissue and bone without recovery of the full function allowed by the original cartilage and, with some devices, serious long-term complications associated with the loss of significant amounts of tissue and bone can cause loosening of the implant. One such complication is osteolysis. Once the prosthesis becomes loosened from the joint, regardless of the cause, the prosthesis will then need to be replaced. Since the patient's bone stock is limited, the number of possible replacement surgeries is also limited for joint arthroplasty.

As can be appreciated, joint arthroplasties are highly invasive and require surgical resection of the entire, or a majority of the, articular surface of one or more bones involved in the repair. Typically with these procedures, the marrow space is fairly extensively reamed in order to fit the stem of the prosthesis within the bone. Reaming results in a loss of the patient's bone stock and over time subsequent osteolysis will frequently lead to loosening of the prosthesis. Further, the area where the implant and the bone mate degrades over time requiring the prosthesis to eventually be replaced. Since the patient's bone stock is limited, the number of possible replacement surgeries is also limited for joint arthroplasty. In short, over the course of 10 to 15 years, and in some cases even shorter time periods, the patient can run out of therapeutic options ultimately resulting in a painful, non-functional joint.

Interpositional knee devices that are not attached to both the tibia and femur have been described. For example, Platt et al. (1969) "Mould Arthroplasty of the Knee," Journal of Bone and Joint Surgery 51B(1):76-87, describes a hemi-arthroplasty with a convex undersurface that was not rigidly attached to the tibia. Devices that are attached to the bone have also been described. Two attachment designs are commonly used. The McKeever design is a cross-bar member, shaped like a "t" from a top perspective view, that extends from the bone mating surface of the device such that the "t" portion penetrates the bone surface while the surrounding surface from which the "t" extends abuts the bone surface. See McKeever, "Tibial Plateau Prosthesis," Chapter 7, p. 86. An alternative attachment design is the Macintosh design, which replaces the "t" shaped fin for a series of multiple flat serrations or teeth. See Potter, "Arthroplasty of the Knee with Tibial Metallic Implants of the McKeever and Macintosh Design," Surg. Clins. Of North Am. 49(4): 903-915 (1969).

Currently available devices do not always provide ideal alignment with the articular surfaces and the resultant joint congruity. Poor alignment and poor joint congruity can, for example, lead to instability of the joint. In the knee joint, instability typically manifests as a lateral instability of the joint.

Thus, there remains a need for compositions for joint repair, including methods and compositions that facilitate the integration between the cartilage replacement system and the surrounding cartilage.

SUMMARY OF THE INVENTION

The present invention provides novel devices and methods for replacing or resurfacing a portion (e.g., diseased area and/or area slightly larger than the diseased area) of a joint or all of a joint (e.g., cartilage and/or bone, one or two articular surfaces) with an implant material, where the implant can achieve a near anatomic fit with the surrounding structures and tissues. In cases where the devices and/or methods include an element associated with the underlying articular bone, the invention also provides that the bone-associated element can achieve a near anatomic alignment with the subchondral bone. The invention also provides for the preparation of an implantation site with a debridement, shaping of the articular surface or subchondral bone, a single cut, or a few relatively small cuts.

Disclosed is a customizable, or patient specific, implant configured for placement between joint surfaces formed by inserting a hollow device having an aperture and a lumen into a target joint, and injecting material into the hollow device to form an implant.

In any of the methods described herein, one or more components of the articular replacement material (e.g., the cartilage replacement material) can be non-pliable, non-liquid, solid or hard. The dimensions of the replacement material can be selected following intraoperative measurements. Measurements can also be made using imaging techniques such as ultrasound, MRI, CT scan, x-ray imaging obtained with x-ray dye and fluoroscopic imaging. A mechanical probe (with or without imaging capabilities) can also be used to select dimensions, for example an ultrasound probe, a laser, an optical probe and a deformable material or device. A surgical navigation system can be used to improve the accuracy of intraoperative placement. Other imaging techniques such as CT or MRI, optionally with near real-time imaging capability can be employed.

In any of the methods described herein, the material or device can be selected (for example, from a pre-existing library of repair systems), grown from cells and/or from various preformed materials, including plastics, polymers, metals. Thus, the material or device can be produced pre- or post-operatively. Furthermore, in any of the methods described herein the material or device can also be shaped (e.g., manually, automatically or by machine), for example using mechanical abrasion, laser ablation, radiofrequency ablation, cryoablation and/or enzymatic digestion. The material or device can also be made using rapid prototyping technology alone or in combination with casting processes. Moreover, the material or device can be made using investment casting if metal alloys are utilized.

In any of the methods described herein, the articular replacement or resurfacing material can comprise synthetic materials (e.g., metals, liquid metals, polymers, alloys or combinations thereof) or biological materials such as stem cells, fetal cells or chondrocyte cells. The articular replacement of resurfacing material can also compromise acellular tissue scaffolds (e.g. collage mesh), that can be optionally seeded with cells prior to, at the time or after the surgery.

In any of the embodiments and aspects described herein, the joint can be any joint in the body such as a knee, hip, ankle, foot joints, shoulder, elbow, ankle, wrist, vertebrae, facet joints, intervertebral disc, etc. In some applications the device can be used to treat conditions outside a joint, for example conditions affecting a vertebral body, non-articular vertebral elements, or paravertebral conditions.

BRIEF DESCRIPTION OF THE DRAWINGS

FIG. 7A shows the y axis as the vertical axis.

FIGS. 11A-G illustrate, in cross-section, the use of a plurality of inflation devices to form an implant. FIG. 11A illustrates a single lumen balloon inserted between two joint surfaces where the inflation occurs within the bounds of the joint. FIG. 11B illustrates another single lumen balloon inserted between two joint surfaces where the inflatable surfaces extend beyond a first and second edge of a joint. FIG. 11C illustrates another single lumen balloon between two joint surfaces. FIG. 11D illustrates a multi-balloon solution using two balloons where the balloons are adjacent to each other within the joint. FIG. 11E illustrates an alternative multi-balloon solution wherein a first balloon is comprised within a second balloon. FIG. 11F illustrates another multi-balloon solution where a first balloon lies within the lumen of a second balloon and further wherein the second balloon is adjacent a third balloon. FIG. 11G illustrates a 3 balloon configuration wherein a first balloon lies adjacent a second balloon and a third balloon fits within the lumen of one of the first or second balloon.

In FIG. 12A the inflation device enables the implant to achieve a surface conforming to the irregularities of the joint surface. In FIG. 12B the inflation device enables the implant to achieve a surface that sits above the irregular joint surface; FIG. 12C illustrates a device formed where a central portion of the device sits above the joint surface irregularities while the proximal and distal ends illustrated form a lateral abutting surface to the joint defects. FIG. 12D illustrates a device formed using a first inflation device within a second inflation device, with an exterior configuration similar to that shown in FIG. 12A; while FIG. 12E illustrates an alternative device formed using at least two different inflation devices having an exterior shape similar to the device shown in FIG. 12C.

DETAILED DESCRIPTION OF THE INVENTION

Figure 1:
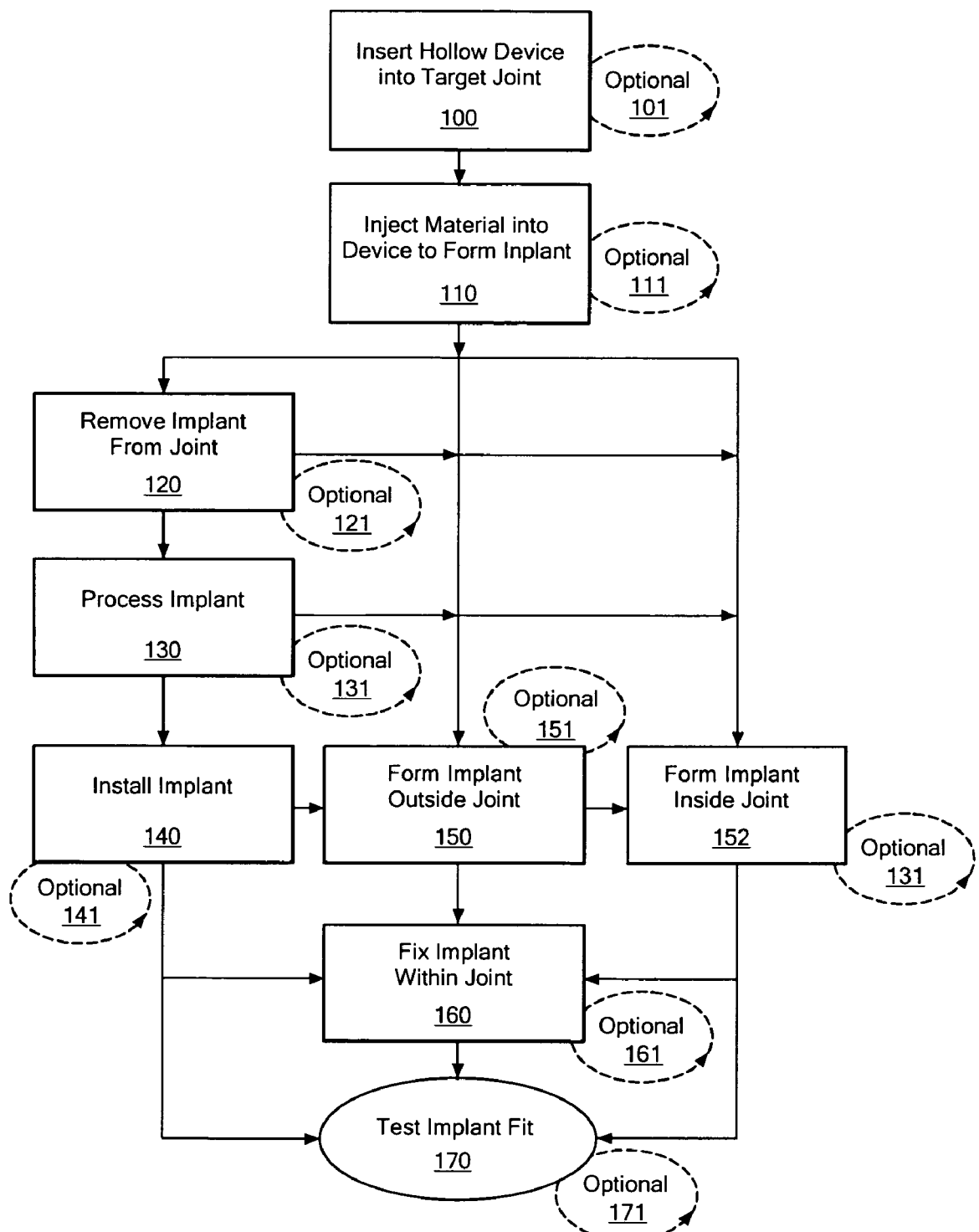
FIG. 1 is a flow chart illustrating steps for forming a device in situ.

The following description is presented to enable any person skilled in the art to make and use the invention. Various modifications to the embodiments described will be readily apparent to those skilled in the art, and the generic principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all issued patents, patent publications, and patent applications cited in this application are incorporated herein by reference.

The present invention provides methods and compositions for repairing joints, particularly for repairing articular cartilage and for facilitating the integration of a wide variety of cartilage or bone repair materials into a subject. The current invention provides, among other things, for minimally invasive methods for partial or complete joint resurfacing or replacement. The methods will require only minimal or, in some instances, no loss in bone stock. Additionally, unlike with current techniques, the methods described herein can help to restore the integrity of the articular surface by achieving an exact or near anatomic match between the implant and the surrounding or adjacent cartilage and/or subchondral bone.

Advantages of the present invention can include, but are not limited to, (i) customization of joint repair, thereby enhancing the efficacy and comfort level for the patient following the repair procedure; (ii) eliminating the need for a surgeon to measure the defect to be repaired intraoperatively in some embodiments; (iii) eliminating the need for a surgeon to shape the material during the implantation procedure; (iv) providing methods of evaluating curvature of the repair material based on bone or tissue images or based on intraoperative probing techniques; (v) providing methods of repairing joints with only minimal or, in some instances, no loss in bone stock; (vi) improving postoperative joint congruity; and (vii) improving postoperative function, for example range of motion.

Thus, the methods described herein allow for the design and use of joint repair material that more precisely fits the defect (e.g., site of implantation) and/or articular surface and/or joint and, accordingly, provides improved repair of the joint.

I. Repair Materials

A wide variety of materials find use in the practice of the present invention, including, but not limited to, plastics, polymers, metals, metal alloys, crystal free metals, ceramics, biological materials (e.g., collagen or other extracellular matrix materials), hydroxyapatite, cells (e.g., stem cells, chondrocyte cells or the like), or combinations thereof. Based on the information (e.g., measurements) obtained regarding the defect and/or the articular surface and/or the subchondral bone, a resurfacing or repair material can be formed or selected. Further, using one or more of these techniques described herein, a cartilage or subchondral bone resurfacing, replacement and/or regenerating material can be applied. The material can have a curvature that can fit into a particular cartilage defect, can follow the contour and shape of the articular surface, and can match the thickness of the surrounding cartilage. The repair material can include any combination of materials, and typically include at least one non-pliable material, for example materials that are not easily bent or changed.

A. Metal and Polymeric Resurfacing or Repair Materials

Currently, joint repair systems often employ metal and/or polymeric materials including, for example, prostheses which are anchored into the underlying bone (e.g., a femur in the case of a knee prosthesis). See, e.g., U.S. Pat. No. 6,203,576 to Afriat, et al. issued Mar. 20, 2001 and U.S. Pat. No. 6,322,588 to Ogle, et al. issued Nov. 27, 2001, and references cited therein. A wide-variety of metals are useful in the practice of the present invention, and can be selected based on any criteria. For example, material selection can be based on resiliency to impart a desired degree of rigidity. Non-limiting examples of suitable metals include silver, gold, platinum, palladium, iridium, copper, tin, lead, antimony, bismuth, zinc, titanium, cobalt, stainless steel, nickel, iron alloys, cobalt alloys, such as Elgiloy®, a cobalt-chromium-nickel alloy, and MP35N, a nickel-cobalt-chromium-molybdenum alloy, and Nitinol™, a nickel-titanium alloy, aluminum, manganese, iron, tantalum, crystal free metals, such as Liquidmetal® alloys (available from LiquidMetal Technologies, www.liquidmetal.com), other metals that can slowly form polyvalent metal ions, for example to inhibit calcification of implanted substrates in contact with a patient's bodily fluids or tissues, and combinations thereof.

Suitable synthetic polymers include, without limitation, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Bioresorbable synthetic polymers can also be used such as dextran, hydroxyethyl starch, derivatives of gelatin, polyvinylpyrrolidone, polyvinyl alcohol, poly[N-(2-hydroxypropyl) methacrylamide], poly(hydroxy acids), poly(epsilon-caprolactone), polylactic acid, polyglycolic acid, poly(dimethyl glycolic acid), poly (hydroxy butyrate), and similar copolymers can also be used.

Other materials would also be appropriate, for example, the polyketone known as polyetheretherketone (PEEK™). This includes the material PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com).

It should be noted that the material selected can also be filled. For example, other grades of PEEK are also available and contemplated, such as 30% glass-filled or 30% carbon filled, provided such materials are cleared for use in implantable devices by the FDA, or other regulatory body. Glass filled PEEK reduces the expansion rate and increases the flexural modulus of PEEK relative to that portion which is unfilled. The resulting product is known to be ideal for improved strength, stiffness, or stability. Carbon filled PEEK is known to enhance the compressive strength and stiffness of PEEK and lower its expansion rate. Carbon filled PEEK offers wear resistance and load carrying capability.

The implant can also be comprised of polyetherketoneketone (PEKK). Other materials that can be used include polyetherketone (PEK), polyetherketoneetherketoneketone (PEKEKK), and polyetheretherketoneketone (PEEKK), and generally a polyaryletheretherketone. Further other polyketones can be used as well as other thermoplastics.

As will be appreciated, other suitable similarly biocompatible thermoplastic or thermoplastic polycondensate materials that resist fatigue, have good memory, are flexible, and/or deflectable have very low moisture absorption, and good wear and/or abrasion resistance, can be used without departing from the scope of the invention.

Reference to appropriate polymers that can be used for the implant can be made to the following documents, all of which are incorporated herein by reference. These documents include: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials.

The substrate can be textured or made porous by either physical abrasion or chemical alteration to facilitate incorporation of the metal coating. Other processes are also appropriate, such as extrusion, injection, compression molding and/or machining techniques. Typically, the polymer is chosen for its physical and mechanical properties and is suitable for carrying and spreading the physical load between the joint surfaces.

More than one metal and/or polymer can be used in combination with each other. For example, one or more metal-containing substrates can be coated with polymers in one or more regions or, alternatively, one or more polymer-containing substrate can be coated in one or more regions with one or more metals.

B. Biological Repair Material

Repair materials can also include one or more biological material either alone or in combination with non-biological materials. For example, any base material can be designed or shaped and suitable cartilage replacement or regenerating material(s) such as fetal cartilage cells can be applied to be the base. The cells can be then be grown in conjunction with the base until the thickness (and/or curvature) of the cartilage surrounding the cartilage defect has been reached. Conditions for growing cells (e.g., chondrocytes) on various substrates in culture, ex vivo and in vivo are described, for example, in U.S. Pat. No. 5,478,739 to Slivka et al. issued Dec. 26, 1995; U.S. Pat. No. 5,842,477 to Naughton et al. issued Dec. 1, 1998; U.S. Pat. No. 6,283,980 to Vibe-Hansen et al., issued Sep. 4, 2001, and U.S. Pat. No. 6,365,405 to Salzmann et al. issued Apr. 2, 2002. Non-limiting examples of suitable substrates include plastic, tissue scaffold, a bone replacement material (e.g., a hydroxyapatite, a bioresorbable material), or any other material suitable for growing a cartilage replacement or regenerating material on it.

Biological polymers can be naturally occurring or produced in vitro by fermentation and the like. Suitable biological polymers include, without limitation, collagen, elastin, silk, keratin, gelatin, polyamino acids, cat gut sutures, polysaccharides (e.g., cellulose and starch) and mixtures thereof. Biological polymers can be bioresorbable.

Biological materials used in the methods described herein can be autografts (from the same subject); allografts (from another individual of the same species) and/or xenografts (from another species). See, also, International Patent Publications WO 02/22014 to Alexander et al. published Mar. 21, 2002 and WO 97/27885 to Lee published Aug. 7, 1997. In certain embodiments autologous materials are preferred, as they can carry a reduced risk of immunological complications to the host, including re-absorption of the materials, inflammation and/or scarring of the tissues surrounding the implant site.

Any biological repair material can be sterilized to inactivate biological contaminants such as bacteria, viruses, yeasts, molds, mycoplasmas and parasites. Sterilization can be performed using any suitable technique, for example radiation, such as gamma radiation.

Any of the biological materials described herein can be harvested with use of a robotic device. The robotic device can use information from an electronic image for tissue harvesting.

In certain embodiments, the resurfacing, repair or replacement material has a particular biochemical composition. For instance, the biochemical composition of the cartilage surrounding a defect can be assessed by taking tissue samples and chemical analysis or by imaging techniques. For example, WO 02/22014 to Alexander describes the use of gadolinium for imaging of articular cartilage to monitor glycosaminoglycan content within the cartilage. The cartilage replacement or regenerating material can then be made or cultured in a manner, to achieve a biochemical composition similar to that of the cartilage surrounding the implantation site. The culture conditions used to achieve the desired biochemical compositions can include, for example, varying concentrations. Biochemical composition of the cartilage replacement or regenerating material can, for example, be influenced by controlling concentrations and exposure times of certain nutrients and growth factors.

II. Devices Design—Device Modeling in Situ

As shown in FIG. 1, the defect repair is modeled in situ. One approach involves inserting a hollow device, such as a balloon, into the target joint 100. Any device capable of accepting, for example, injections of material would be suitable. Suitable injection materials include, for example, polymers and other materials discussed in Section I, above, can be used without departing from the scope of the invention. Other suitable materials could also be used without departing from the scope of the invention.

In one embodiment it is contemplated that an insertion device has a substantially fixed shape that matches at least one articular surface or subchondral bone of the joint. After inserting the insertion device 100, material is injected into the joint through the insertion device 110 where it then hardens in situ, forming an implant 152. The injection material can optionally bond to the device while hardening.

Alternatively, the implant can be removed after hardening 120 for further processing 130, such as polishing, e.g. as described Section III.

Where the implant is removable after hardening in situ, it can be preferable to have the implant be formed so that it is collapsible, foldable or generally changeable in shape to facilitate removal. After processing, the implant can be reinstalled 140.

The insertion device can be composed of a plurality of subcomponents. The different subcomponents can be connected or assembled prior to insertion into the articular surface that substantially within the body), or metals can be assembled after insertion to the joint 152. The insertion device and/or one or more of its subcomponents can be disassembled inside the joint, or adjacent the joint our outside the joint. Optionally, the insertion device and/or one or more of its subcomponents can remain in the joint, adjacent to the joint or outside the joint after the procedure, or it can be removed from the joint before, during and after the procedure.

Additionally, the implant can be fixed to the surface of the bone after implantation 160. For example, fixation mechanisms can include mechanical structures such as fins, keels, teeth, pegs, pins or screws or bone cement, etc. Typically after the device is implanted and/or optionally fixed within the joint, the functionality of the implant is tested 170 to determine whether it enables the joint to engage in a desired range of motion. As will be appreciated by those of skill in the art, one or more of these steps can be repeated without departing from the scope of the invention, as shown by the optional repeat steps 101, 111, 121, 131, 141, 151, 153, 161 and 171.

In other embodiments, portions of the insertion device can be rigid, or substantially rigid, while other portions of the device are deformable or malleable. Alternatively, a portion of the device can be relatively more rigid than another portion, without any requirement that any section be rigid, deformable or malleable, but that sections vary in hardness relative to another section. In this manner the shape of the rigid, substantially rigid, or relatively more rigid section can be determined. In this manner, it is possible to influence the degree of conformity of the repair, resurfacing or replacement material to the articular surface, articular features or subchondral bone or surrounding bone. For example, the malleable, deformable, or relatively more deformable portion of the implantation device can then take the shape of one or more articular surfaces in situ. This occurs particularly after the repair, resurfacing or replacement material has been injected and while the material is hardening in situ. In still other embodiments, the entire device can be deformable.

In other embodiments, the implantation device can be expandable or collapsible. For example, a support structure such as a Nitinol™ mesh can be inserted into the joint. Insertion can occur via, for example, a catheter or an arthroscopy portal.

In other embodiments, the repair, resurfacing or replacement material can be self-expandable and inserted into the joint, for example using a catheter. Once in situ, the repair, resurfacing or replacement material can expanded and be placed or left adjacent to one or more articular surface. The repair, resurfacing or replacement material can be optionally anchored to the articular surface(s) or underlying or adjacent bone Once inside the joint, the implantation device can then be expanded. The implantation device can include a receptacle, such as a bag, to receive the injection of hardening material, such as polyethylene or other liquid including metal preparations. The receptacle portion of the implantation device can be bio-resorbable and/or can bond with the injected material. Alternatively, the implantation device can be removed subsequent to injecting the material. Where a supporting material is used, the supporting material can be removed concurrently or subsequent to the removal of the implantation device, either via an incision or by collapsing the implantation device and removing it via, for example, the catheter or arthroscopy portal.

In another embodiment, a balloon such as that shown in FIGS. 11A-E, can be used as the implantation device. Different balloon shapes and sizes can be made available. A detailed description of all possible shapes and sizes for the balloons is not included to avoid obscuring the invention, but would be apparent to those of skill in the art. Where a balloon is used, it can be inserted into a joint and inflated. The size, height, shape and position of the balloon can be evaluated radiographically, fluoroscopically, arthroscopically or via an open incision or using, for example, an imaging test relative to the articular surface and the other articular strictures. Range of motion testing can be performed in order to ensure adequate size, shape and position of the device.

Figure 11A:
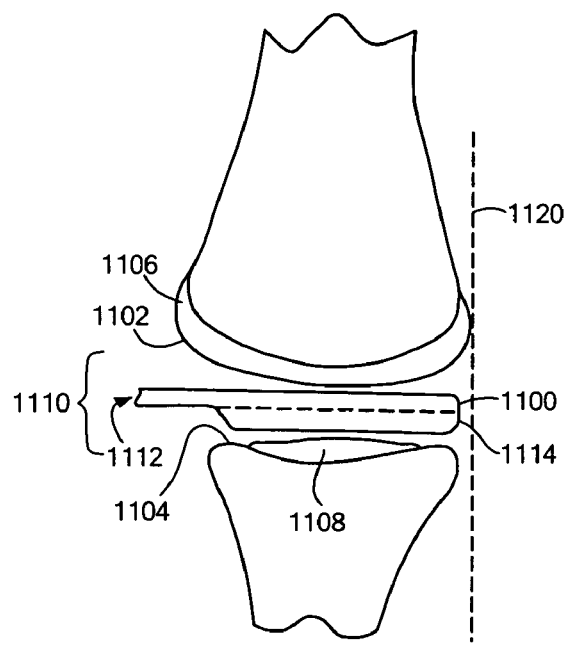

After insertion, the balloon can be injected with, for example, a self-hardening material, or material that hardens upon activation. Suitable materials are described below and would be apparent to those of skill in the art. Typically, upon injection, the material is in a fluid or semi-fluid state. The material expands the balloon as it is injected which results in the balloon taking on the shape of the articular surface, for example as shown in FIG. 11A, and other articular structures such that it fills the defect.

The balloon can be slowly injected with a self hardening or hardening material such as a polymer and even metals. The material is initially in a fluid or semi-fluid state. The material expands the balloon whereby the shape of the balloon will take substantially the shape of the articular surface(s) and other articular structures. The polymer will subsequently harden inside the balloon thereby substantially taking the shape of the articular cavity and articular surface(s)/structures. The balloon can also be composed of a bio-resorbable material. The balloon can also be removed after the procedure.

Figure 2:
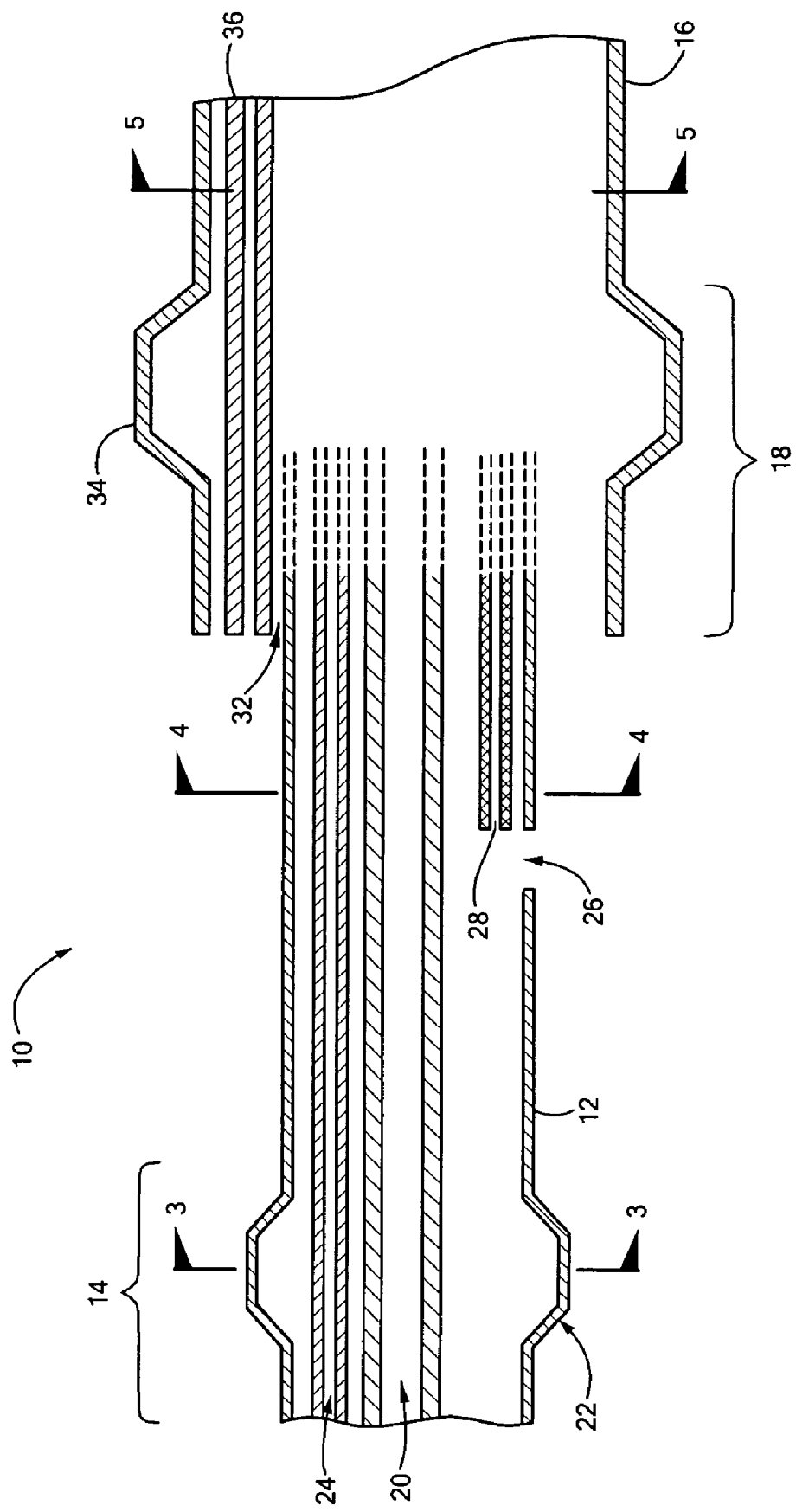
FIG. 2 is a partial cross-sectional view of an inflation device assembly.

Referring now to the drawings, wherein similar parts are identified by like reference numerals, FIG. 2 illustrates an inflation device assembly 10. Inflation device assembly 10 is intended to broadly include any medical device designed for insertion into a physiological space or lumen to permit injection and/or withdrawal of fluids, to maintain the patency of the lumen, or for any other purpose. It is contemplated that the apparatus has applicability for use with any physiological lumen or space where forming a device in situ is desired.

Inflation device assembly 10 includes a first tube 12 having a proximal end (not illustrated) and distal end 14, and a second tube 16, having a proximal end (not illustrated) and a distal end 18. The second tube 16 is telescopically disposed over the first tube 12.

The first tube 12 can include a lumen 20 for allowing first tube 12 to be fed over and maneuvered over a navigation device, such as a guidewire. A first balloon 22 is disposed on distal end 14. First balloon 22 is selectively inflatable to dilate from a collapsed configuration to a desired and controlled expanded configuration. First balloon 22 can be selectively inflated by supplying a fluid into a first inflation lumen 24 at a predetermined rate of pressure, for example 1-20 atm. The fluid can be radioopaque for visualization using x-ray imaging including fluoroscopy. First balloon 22 is also selectively deflatable, after inflation, to return to the collapsed configuration or a deflated profile. In one embodiment, first tube 12 can include a port 26 in fluid communication with port lumen 28. Port 26 allows for injection or withdrawal of fluids through port lumen 28. Port 26 can be embodied by many different types of openings such as, but not limited to, holes, slits, annual gaps, porous membranes and osmotic filters.

Figure 5:
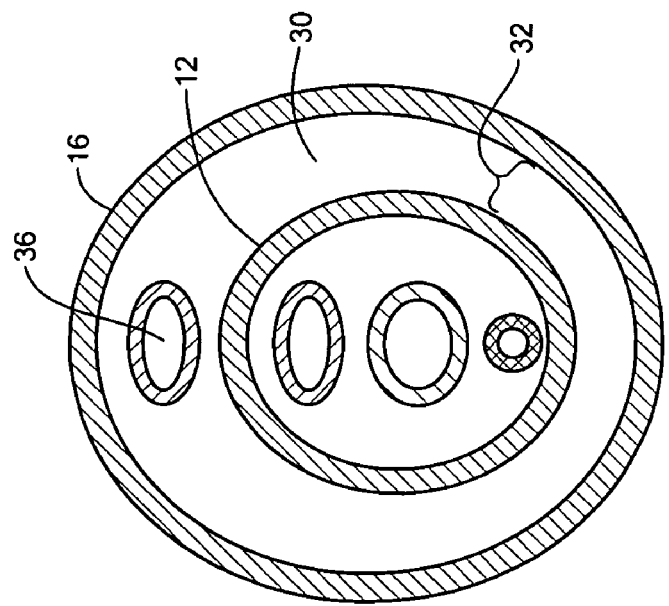
FIG. 5 is cross-sectional view taken along the lines 5-5 in FIG. 2.
Figure 4:
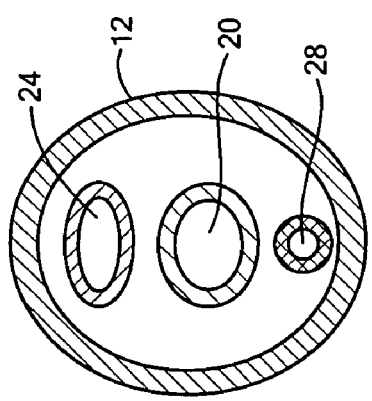
FIG. 4 is a cross-sectional view taken along the lines 4-4 of FIG. 2.
Figure 3:
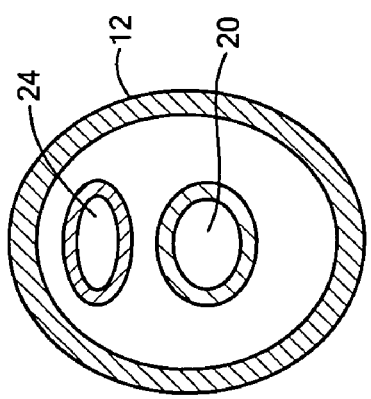
FIG. 3 is a cross-sectional view taken along the lines 3-3 in FIG. 2.

Referring to FIGS. 3, 4, and 5, second tube 16 includes a central lumen 30 sized so as to slidably receive first tube 12, but large enough so as to create an annular gap 32 between the outer surface of first tube 12 and the inner surface of central lumen 30. The space between the surfaces can, for example, be from about 0.05 mm to about 1.0 mm. Annular gap 32 functions as a second port which additionally allows for injection or withdrawal of fluids by a user. A second balloon 34 is disposed on distal end 18 and is in fluid communication with an inflation lumen 36. Second balloon 34 performs a similar function to that of first balloon 22 and can be sized to have the same outer diameter in the desired inflated state. The inflation of first and second balloons 22 and 34 create a treatment space for the application of a therapeutic substance prior to placing an inflation device for forming a device in situ with the treatment space. Annular gap 32 used in conjunction with port 26 can also provide for the withdrawal of the bodily fluids, application of a therapeutic substance, and the re-circulation and application of the substance in the treatment space for maintaining the concentration of the therapeutic substance at a therapeutically acceptable level for a selected duration of time.

First and second balloons 22 and 34 can be made from any suitable material, including, but not limited to, polymers and copolymers of polyolefins, polyamides, polyesters and the like. The specific material employed must be mutually compatible with the fluids employed in conjunction with balloons 22 and 34 and must be able to stand the pressures that are developed therein. The balloons 22 and 34 can have any suitable wall thickness and/or dimensions so long as the thickness and/or dimensions do not compromise properties that are critical for achieving optimum performance. The properties include high burst strength, low compliance, good flexibility, high resistance to fatigue, the ability to fold, the ability to cross and recross a desired region of treatment or an occluded region in a lumen, and low susceptibility to defect caused by handling. The properties include also fit to the articular surface, the subchondral bone, the surrounding bone or other articular structures including ligaments. By way of example, and not limitation, the thickness can be in the range of about 10 microns to about 200 microns, the diameters of balloons 22 and 34 in the expanded configuration can be in the range of about 2 mm to about 70 mm and the lengths can be in the range of about 2 mm to about 70 mm, the specific specifications depending on the procedure and the joint for which balloons 22 and 34 are to be used and the anatomy and size of the target lumen in which the balloons are to be inserted.

In accordance with another embodiment of the invention, first or second balloons 22 and 34 can also be used to deliver a therapeutic substance to the treatment space should either of balloons 22 and 34 be embodied so as to include a porous membrane or one or more openings for release of the therapeutic substance. A therapeutic substance can be included in the fluid that is used to inflate balloons 22 or 34. To more effectively deliver a therapeutic substance to the treatment space, the balloon membrane can be exclusively porous or can have exclusively openings on the portion of the membrane that faces the treatment space.

One of ordinary skill in the art can appreciate that any number of balloons can be included with the first or second tubes 12 and 16. Such balloons can be strategically placed so as to serve its intended function, such as device placement.

In another embodiment, an ultrasonic transducer and/or an electrode element (not shown) can be carried by, for example, tube 12. Use of the ultrasonic transducer or electrode element is advantageous because tissue temperature and capillary and cellular permeability may be increased. These results may enhance intra-tissue transport of a substance, and enhance cellular uptake.

Figure 6:
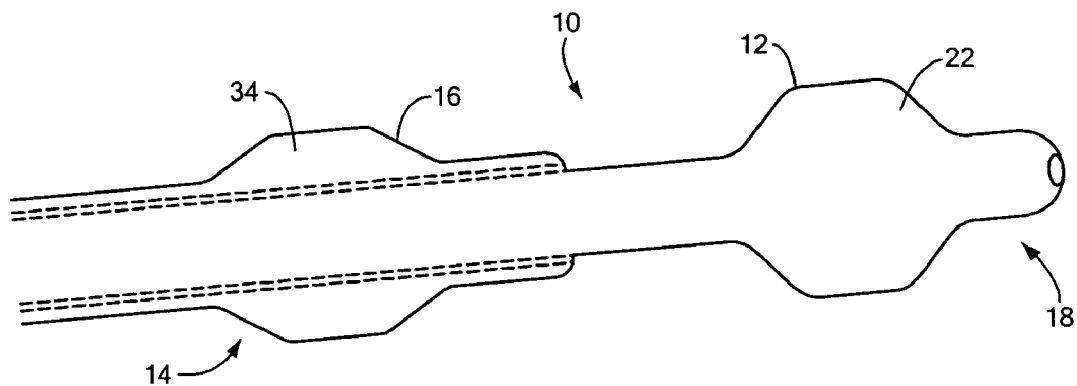
FIG. 6 is a perspective view of an inflation device according to the invention.
Figure 7A:
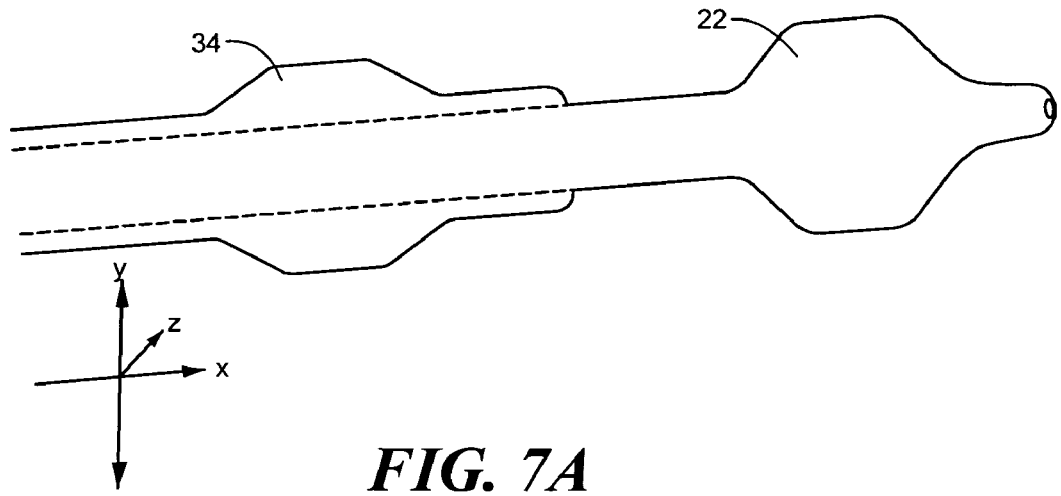
FIGS. 7A and B are a cross-sectional views of an inflation device.
Figure 7B:
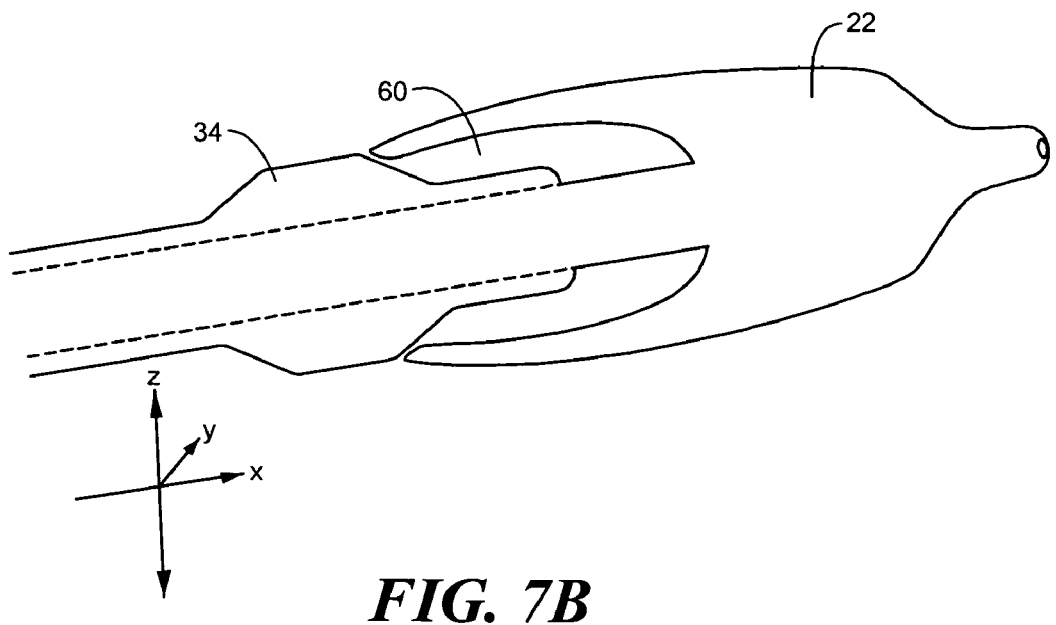
FIG. 7B shows the z axis as the vertical axis.
Figure 8:
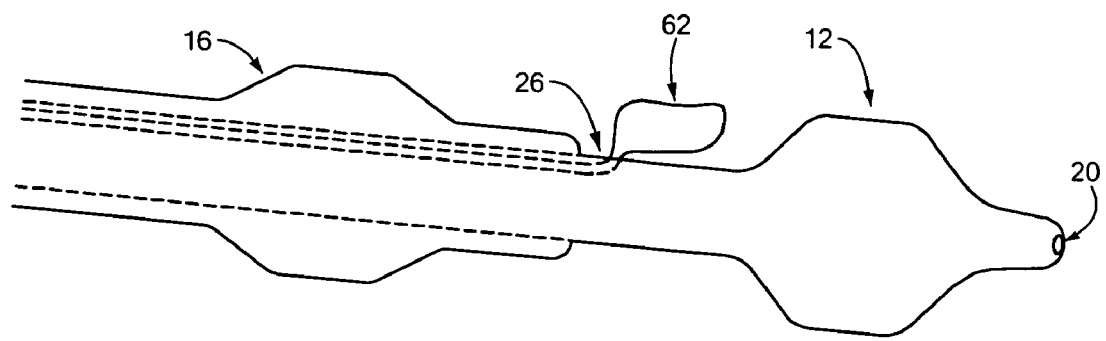
FIG. 8 is a perspective view of an inflation device according to the invention.

Turning now to FIG. 6, a perspective view of the inflation device 10 is shown. The distal end 18 of the first tube 12 is shown with the balloon 34 inflated. The second tube 16 has been slidably placed over the first tube 12. FIG. 7 illustrates alternate embodiments of the balloon 22 of the first tube 12. As shown in FIG. 7A, in a first orientation, the balloon 34 extends outward in a radial fashion away from the central axis of the inflation device 10. When rotated 90 degrees, the balloon extends outwardly in a radial fashion but also forms backward extending wings 58, thus creating a space 60 between the first and second balloons 22, 34. As will be appreciated by those of skill in the art, the balloons 22, 34 can be configured so that the second balloon 34 forms wings that extend forward toward the first balloon 22 to create space 60. Alternatively, the balloons 22, 34 can be configured such that the profile in both axis are as shown in either FIG. 7A or FIG. 7B, Turning now to FIG. 8, a first tube 12 and a second tube 16, with a third tube 62 extending out from the port 26 located on the first tube 12.

Figure 9:
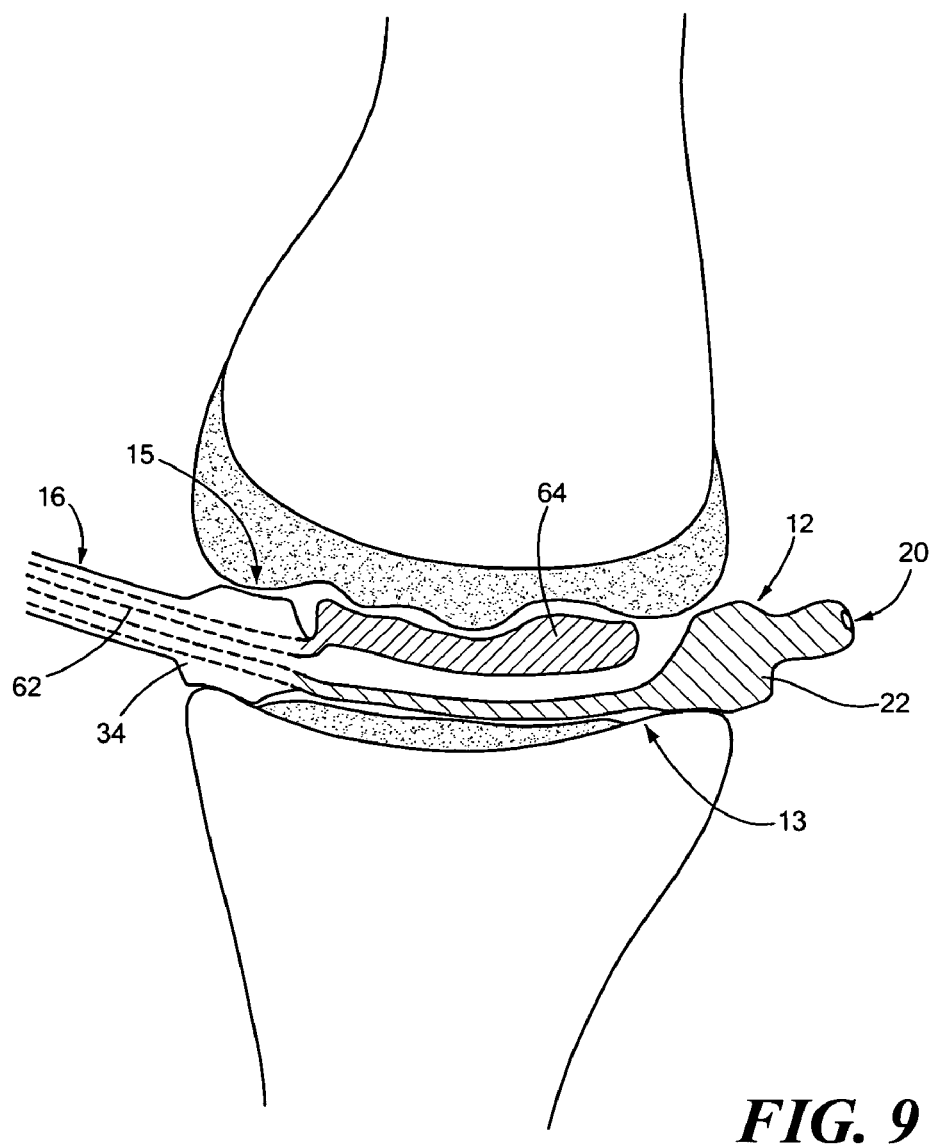
FIG. 9 is a cross-sectional view of an inflation device of the invention in situ.

FIG. 9 illustrates one configuration of the invention inserted between the femur and the tibia in a knee joint. As illustrated, the first tube 12 is extended through the joint space to a distal end of the joint, relative to the position of the physician advancing the tube, and a second tube 16 is advanced over the first tube 12. Each tube is inflated such that its balloon surfaces contact surfaces of the joint, e.g. on the tibial side 13 and the femoral side 15. After the balloon portions 22, 34 of the tubes 12, 14 are inflated, a third tube 62 is advanced through a lumen such that it sits between the first and second tube 12, 14 in the space created by the balloons 22, 34 thereof. The balloon 64 of the third tube 62 is then inflated to conform to the surfaces of the femur and tibia and to conform to any defects on the surfaces of the tibia and/or the femur. The tubes can be shaped to extend over portions, most or all of the articular surface. For example, they can be relatively flat (e.g. 1-3 mm in height) relatively wide (e.g. 2-5 cm in width) and relatively long (e.g. 2-5 cm in length).

Figure 10:
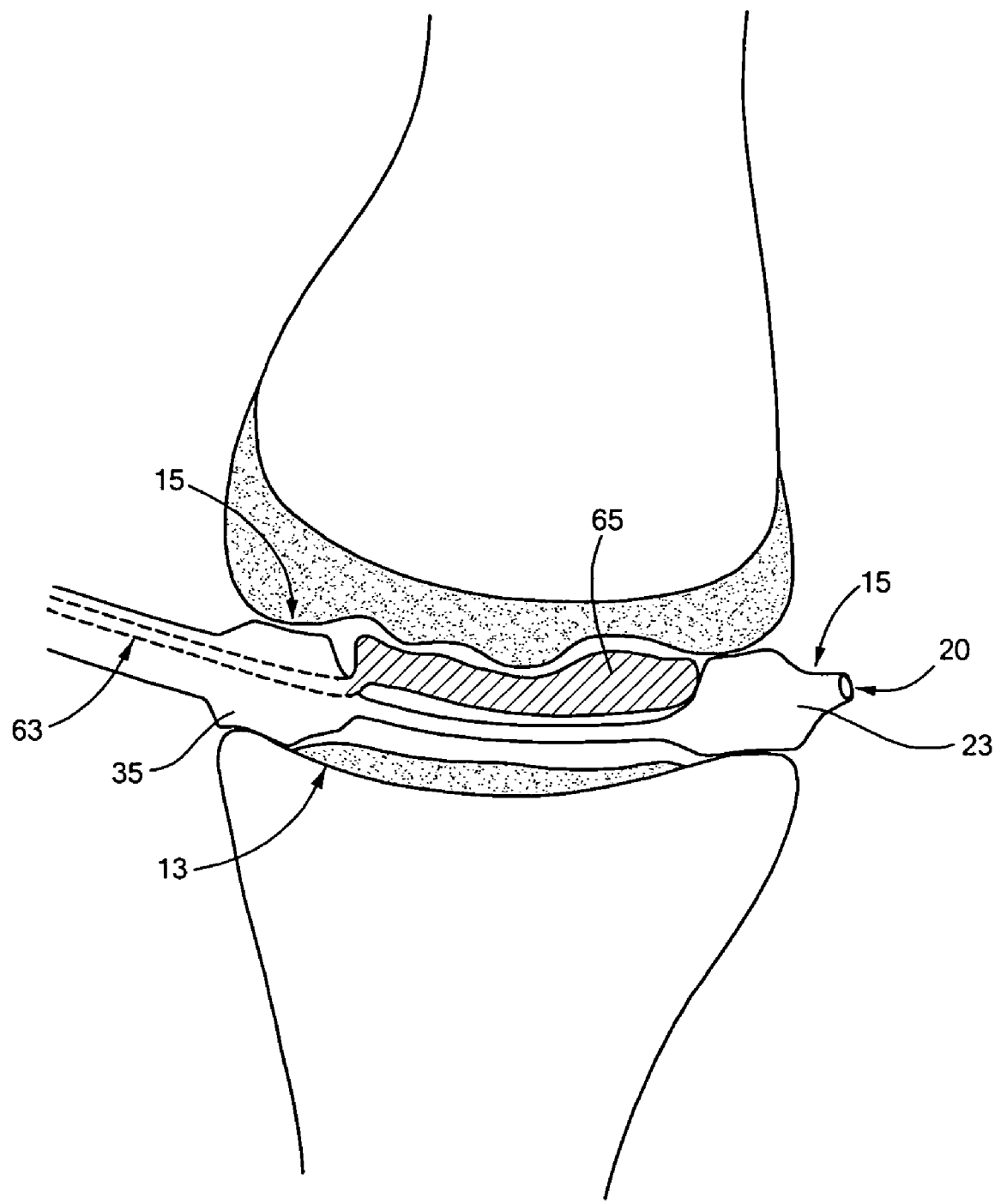
FIG. 10 is a cross-sectional view of an alternate embodiment of an inflation device of the invention in situ.

FIG. 10 illustrates another configuration of the invention inserted between the femur and the tibia in a knee joint. As illustrated, the first tube 11 is extended through the joint space to a distal end of the joint, relative to the position of the physician advancing the tube. The first tube depicted in this figure has two balloon portions 23, 35. The tube is inflated such that its balloon portions 23, 35 expand and contact surfaces of the joint, e.g. on the tibial side 13 and the femoral side 15. After the balloon portions 22, 34 of the tubes 12, 14 are inflated, a second tube 63 is advanced through a lumen such that it sits between the balloon portions 23, 35 of the first tube 11. The balloon 65 of the second tube 63 is then inflated to conform to the surfaces of the femur and tibia and, optionally, to conform to any defects on the surfaces of the tibia and/or the femur.

Figure 11B:
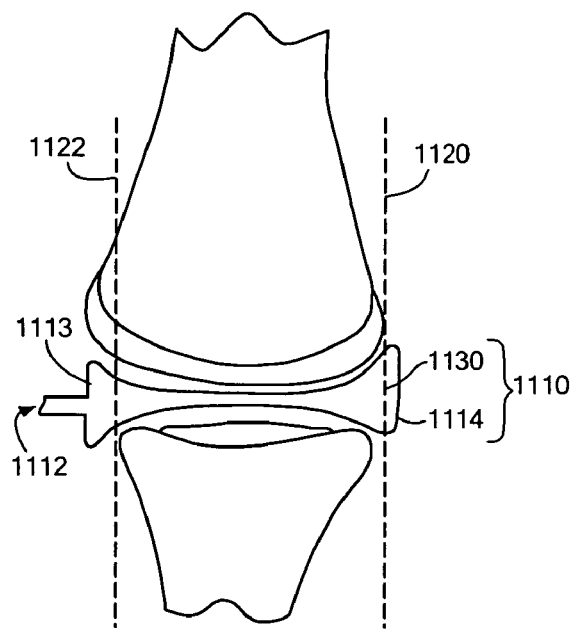
Figure 11C:
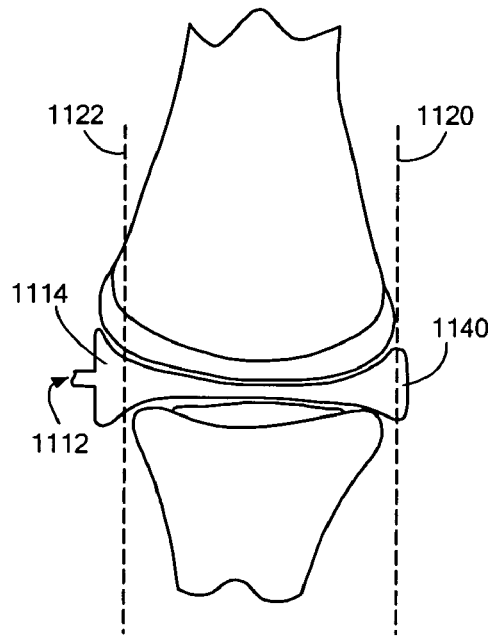
Figure 11D:
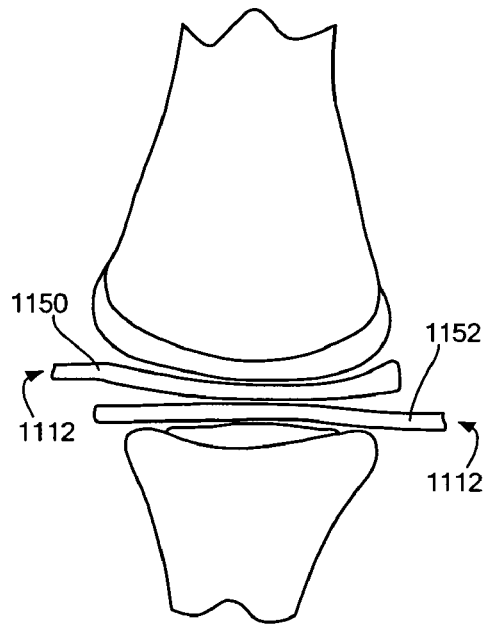
Figure 11G:
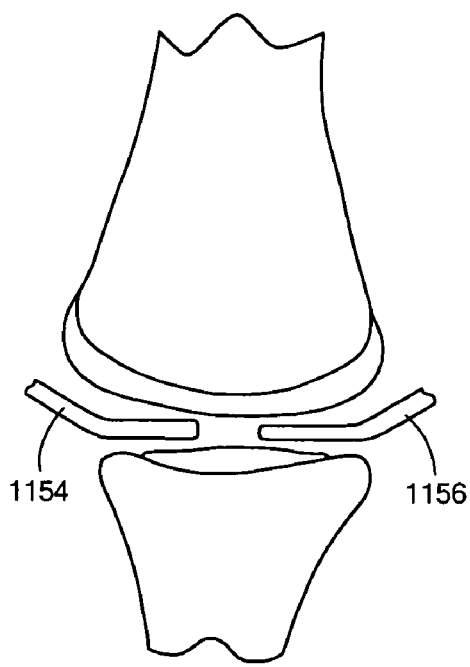
Figure 11G:
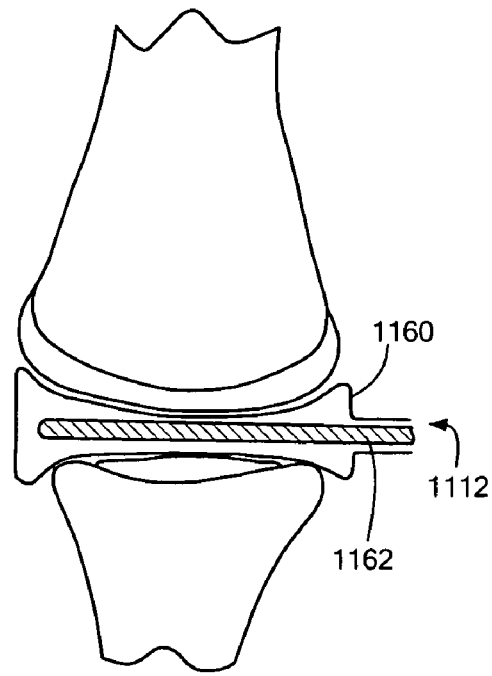
Figure 11G:
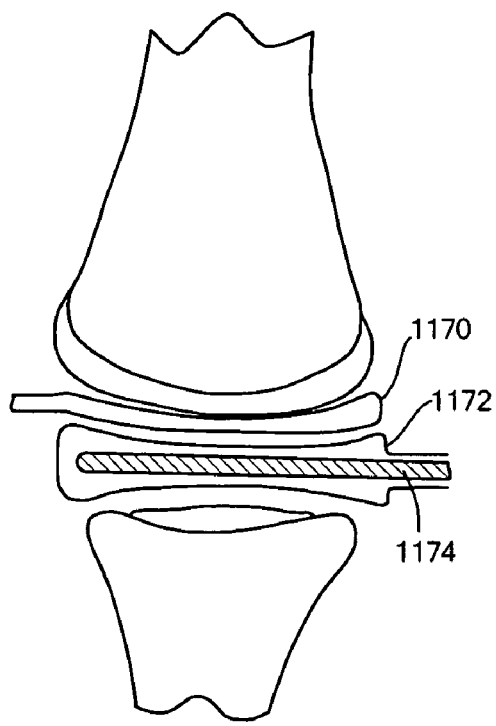

Comparing, for example, the embodiments illustrated in FIGS. 11A-C, FIG. 11A illustrates a single balloon 1100 inserted between two joint surfaces 1102, 1104 of a joint 1110. In this figure, the joint surfaces are illustrated with associated cartilage 1106, 1108. The proximal end 1112 of the balloon is configured to communicate with a device that enables the balloon to be inflated, e.g. by filling the balloon 1100 with a substance. Substances include, but are not limited to, air, polymers, crystal free metals, or any other suitable material, such as those discussed in Section I above. The balloon 1100 of FIG. 11A is configured such that the distal end of the balloon 1114 does not extend beyond distal end of the joint 1120 (where the distal end of the joint is defined relative to the area of the joint where the balloon entered the joint).

FIG. 11B illustrates an alternative balloon 1130 wherein the distal end 1114 of the balloon 1130 and the proximal end 1113 of the balloon 1130 extends beyond the distal 1120 and proximal 1122 end of the joint. This extension can be optimized for flexion and extension by using different balloon sizes. Moreover, this extension can be modified by using balloons with varying elasticity across the balloon surface or wall. For example, the central portions of the balloon can be more rigid than the peripheral portions thereby facilitating the formation of the extensions, for example with increasing balloon pressures. The extensions can be limited to the intraarticular space. Optionally, however, one or more extensions can extend outside the joint capsule or can be located, at least in part, in the extraarticular space. FIG. 11C illustrates a balloon 1140 wherein the balloon 1140 is configured such that the distal end 1114 of the balloon 1140 extends beyond the distal 1120 of the joint while the proximal end 1114 of the balloon 1140 does not extend beyond the end of the joint. As will be appreciated by those of skill in the art, other permutations are possible without departing from the scope of the invention.

Additionally, a sharp instrument such as a scalpel can be inserted into the balloon or adjacent to the balloon and the balloon can be cut or slit. The balloon can then be pulled back from the hardened material and removed from the joint, preferably through a catheter or an arthroscopy portal. Alternatively, the balloon can be bioresorbable.

More than one balloon can be used as illustrated in FIGS. 11D-G. Where a plurality of balloons used, the balloons can be configured such that the balloons are inserted side-by-side as shown by 1150, 1152 in FIG. 11D, inserted in different compartments as shown by 1154, 1156 in FIG. 11E, one or more balloons are encompassed within the lumen of another balloon, as shown by 1160, 1162 and 1170, 1172, 1174 in FIGS. 11F-G, in a top-bottom relationship, and/or combinations thereof. In this manner, two or more repair, resurfacing or replacement devices can be formed in situ and these can be, optionally, slidingly engaged so as to form a mobile bearing surface.

Each balloon can have the same or different wall thickness or can be composed of the same or different materials. As a result of differences in material, a person of skill in the art will appreciate that the amount of pressure or force required to expand each of the balloons can vary either uniformly or in a non-uniform fashion. These pressures would be known to a person of skill in the art and are not discussed at length herein to avoid obscuring the invention.

For example, in one scenario the superior and inferior surface of a first, inner balloon, can have a low inflation pressure relative to a second balloon. Thus, as the material is injected, the pressure created inside the lumen of the balloon is directly transmitted to one or more articular surface. In this manner, the distance between the two articular surfaces can be controlled and a minimum distance can be obtained ensuring a sufficient thickness of the resultant implant. This embodiment can be useful in areas within or bordering the contact zone of the articular surface.

A second outer or peripheral balloon can be provided that requires a higher inflation pressure relative to the first balloon. The inner, low inflation pressure balloon can be placed in the weight-bearing zone. The same balloon can also have different wall properties in different regions of the balloon, e.g. a rigid wall with high inflation pressures in the periphery and a less rigid wall with intermediate or low inflation pressures in the center.

Alternatively, a first balloon, having a low inflation pressure relative to a second balloon is provided in an area bordering the contact zone of the articular surface. Again, as material is injected, the pressure created inside the lumen of the balloon is directly transmitted to one or more articular surface. In this manner, the distance between the two articular surfaces can be controlled and a minimum distance can be obtained ensuring a sufficient thickness of the resultant implant.

A second balloon can be provided at an area where there is relatively more weight bearing. This balloon can be configured to require a higher inflation pressure relative to the first balloon.

Differences in wall thickness, pressure tolerances and expandability of balloons can also be used to influence the resulting shape of the injected material.

Figure 12A:
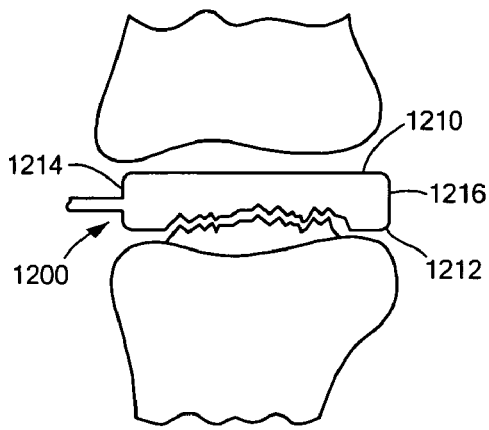
FIGS. 12A-E illustrate a variety of cross-sectional shapes achieved using balloons with variable wall thicknesses or material compositions.

The results of using inflation devices, or balloons, with differing wall thicknesses or pressure tolerances is shown in FIGS. 12A-F. As shown in FIG. 12A the balloon 1200 has an upper surface 1210 and a lower surface 1212 along with a proximal end 1214 and a distal end 1216. The relative pressure tolerance of the balloon or inflation device 1200 is lower on the lower surface 1212 than the upper surface 1210. As a result, the upper surface of the balloon 1210 has a relatively flat configuration relative to its corresponding joint surface while the lower surface 1212 has a relatively conforming shape relative to its corresponding joint surface.

Figure 12B:
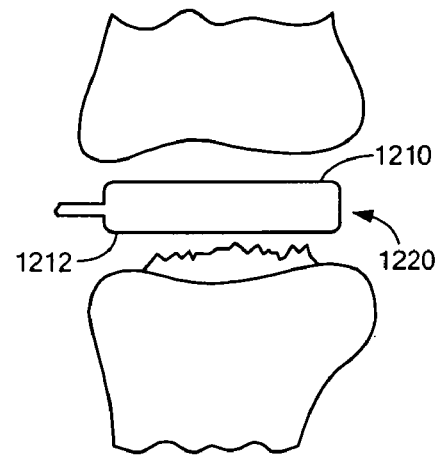

Turning now to FIG. 12B, the inflation device used 1220 has a relatively constant pressure tolerance that is relatively high which results in both the upper surface 1210 and the lower surface 1212 having relatively flat configurations relative to each of its corresponding joint surfaces, regardless of the joint surface anatomy.

Figure 12C:
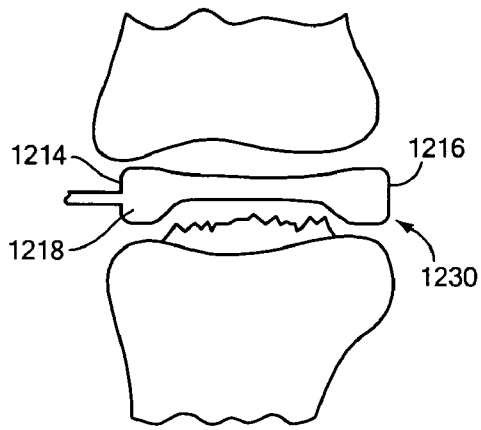

FIG. 12C illustrates a balloon 1230 having a low inflation pressure at its proximal 1214 and distal 1216 ends, with a higher inflation pressure at a central region 1218. The result of this configuration is that when the balloon is inflated, the proximal and distal ends inflate to a greater profile (e.g., height) than the central region. The inflation pressure of the central region, although higher than the proximal and distal ends, can be set such that the central region has a relatively flat configuration relative to the corresponding joint surfaces, as shown, or can be configured to achieve the result shown in FIG. 12A.

As will be appreciated by those of skill in the art, any of these balloons can be configured to have varying properties resulting in portions of the wall being less rigid than other portions, within the same balloon, e.g. a rigid wall with high inflation pressures in the periphery and a less rigid wall with intermediate or low inflation pressures in the center. Where there is more than one thickness to the balloon, it could, for example, have less stiffness anteriorly; greater stiffness centrally, and less stiffness posteriorly. The wall thickness variability will enable the device to accommodate shape formation. Central thickness will help prevent the device from fully conforming to the irregular surface of the joint, which may be important where there are irregularities to the joint surface, such as bone spurs. Alternatively, if the central portion is of less stiffness than the anterior and posterior sections, the device would be configured to conform more closely to the shape of the joint surface, including any irregularities. The closer the device conforms to the joint shape, the more the device seats within the joint.

Optionally, the surgeon can elect to remove surface irregularities, including bone spurs. This can be done using known techniques such as arthroscopy or open arthrotomy.

Shape and size of the implantation device used can be selected to achieve an optimal fit for a patient and a particular joint. Selection can be made preoperatively, for example using imaging or intraoperatively.

Where more than one balloon is used, the different balloons can have different shapes and sizes. Shape and size can be adjusted or selected for a given patient and joint. In addition to size and shape differences of the balloons, each of the balloons can also be configured to have different and/or varying wall thicknesses. For example, one balloon could be configured with a central portion that is less stiff than the anterior and posterior sections while a second balloon could be configured so that the central portion is of greater stiffness than the anterior and posterior section.

Figure 12D:
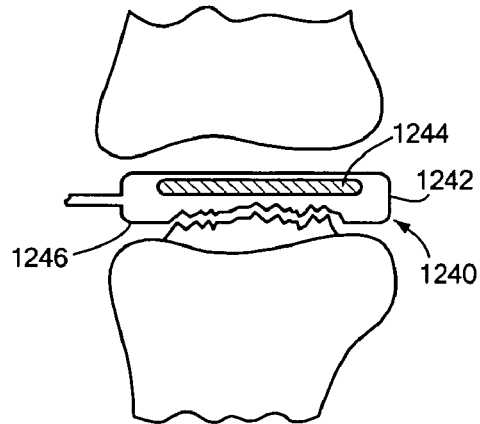
Figure 12E:
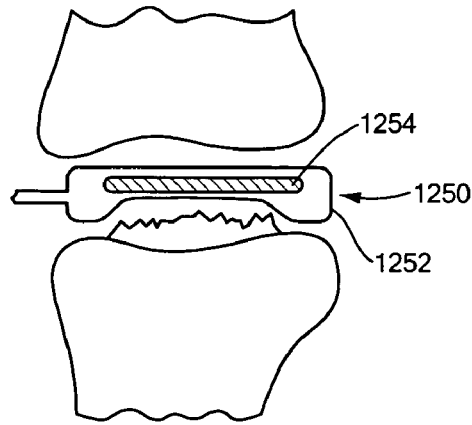
Figure 13:
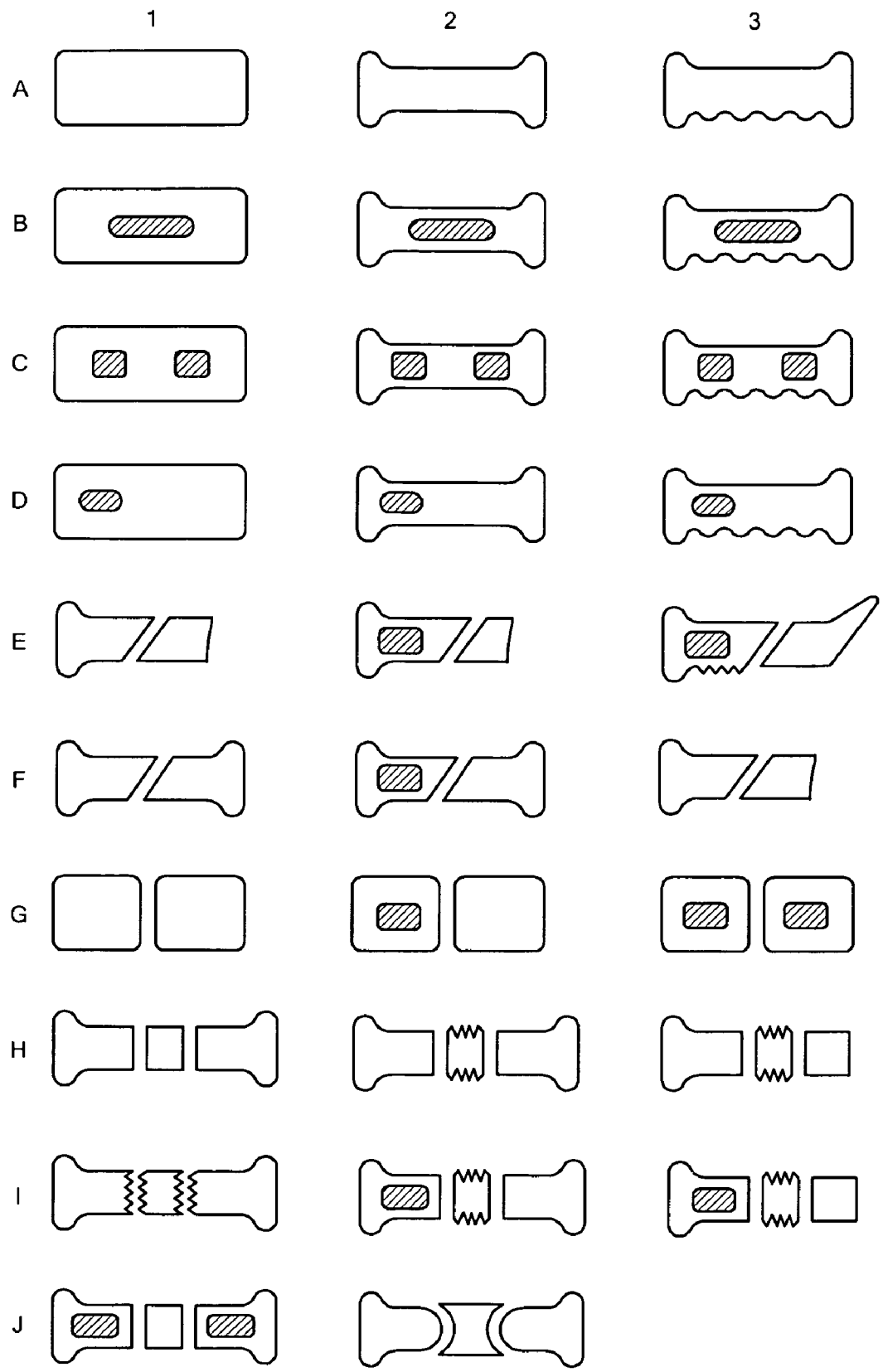
FIGS. 13A-J(1-3) show a variety of cross-sectional views of the inflation devices shown, for example, in FIGS. 11 and 12 taken at a position perpendicular to the views shown in FIGS. 11 and 12.

FIGS. 12D-E illustrate configurations using two balloons. As shown in FIG. 12D the first balloon 1244 sits within a second balloon 1242 to form an inflation device 1240. In this embodiment, the inferior surface 1246 of the external second balloon 1242 is configured with an inflation pressure that enables at least one surface of the device to conform, or substantially conform, to the corresponding joint surface. FIG. 12E also illustrates a two balloon configuration 1250 with a first balloon 1254 and a second balloon 1252. In this embodiment, the inflation pressure of the device is configured such that the surface conforms to the overall shape of the corresponding joint surface, but does not conform to cartilage or bone defects, thereby bridging the defects.

FIGS. 13A-J(1-3) illustrate a variety of cross-sections possible for the embodiments shown in FIGS. 11-12. These embodiments illustrate possible profiles achieved with a single balloon (FIGS. 13A(1-3)); a dual balloon embodiment wherein one balloon fits within a second balloon in approximately a central position (FIG. 13B(1-3)) or in an off-centered position within a second balloon (FIGS. 13D(1-3)); a tri-balloon set-up where two balloons fit within a first balloon (FIGS. 13C(1-3)), three balloons are positioned next to each other (FIGS. 13H(1-3)), or two balloons are adjacent each other while one balloon has another balloon within its lumen (FIGS. 13E(2-3), F(2), G(2)); a four balloon set-up where two balloons are adjacent each other and each one has a balloon within its lumen (FIG. 13G(3)) or three balloons are adjacent each other with at least one of the three balloons having another balloon within its lumen (FIGS. 13I(2-3)), or a five balloon set up where three balloons are positioned adjacent each other and two of the three balloons have balloons within its lumen (FIG. 13J(1)). As will be appreciated by those of skill in the art, other combinations and profiles are achievable using the teachings of the invention without departing from the scope of the invention. All possible combinations have not been illustrated in order to avoid obscuring the invention.

In another embodiment, a probe can be inserted into the balloon or the device. The probe can be utilized for measuring the device thickness (e.g. minima and maxima). In this and other embodiments, the balloon can be initially injected with a test material that is typically not hardening. Once inside the balloon or the device, the thickness of the device or the balloon can be measured, e.g. for a given inflation pressure. In this manner, a sufficient minimum implant thickness can be ensured. Probes to measure the thickness of the device or the balloon include, but are not limited to ultrasound, including A-, B- or C-scan.

The foregoing description of embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated. It is intended that the scope of the invention be defined by the following claims equivalents thereof.

What is claimed is:

1. A customizable implant configured for placement between joint surfaces of a joint, the implant comprising:
    an expandable body;
    a hollow cavity within said body;
    a first exterior surface portion for opposing a first joint surface;
    a second exterior surface portion for opposing a second joint surface;
    the first exterior surface portion being substantially flat relative to the first joint surface;
    the second exterior surface portion substantially matching a contour of the second joint surface; and
    wherein the implant is configured for placement between the joint surfaces such that when expanded the second exterior surface portion engages the second joint surface and the first exterior surface portion provides the joint with a range of motion.

2. The implant of claim 1, wherein at least a portion of the implant is configured based on patient-specific data.

3. The implant of claim 1 having a first exterior surface portion configuration based on patient-specific data.

4. The implant of claim 1 having a second exterior surface portion configuration based on patient-specific data.

5. The implant of claim 1, wherein the second exterior surface portion is shaped and/or formed so that when expanded, the second exterior surface substantially conforms with the second joint surface.

6. The implant of claim 1, wherein the joint is selected from the group consisting of facet joints, uncovertebral joints and costovertebral joints.

7. The implant of claim 1, wherein the implant is fixable within the joint.

8. The implant of claim 1, wherein the body consists of different materials.

9. The implant of claim 1, wherein the body has a variable stiffness.

10. The implant of claim 1, wherein the first exterior portion is curved.

11. The implant of claim 1, wherein the implant is expandable to a size sufficient to surround a defect within the joint when implanted between the joint surfaces.

12. The implant of claim 1, wherein the implant is expandable to a size sufficient to extend beyond at least one perimeter of the joint when implanted between the joint surfaces.

13. The implant of claim 1, wherein the implant is expandable to a size sufficient to engage a joint surface along its perimeter when implanted between the joint surfaces.

14. The implant of claim 1, wherein the implant is expandable to a size sufficient to engage at least one joint surface when implanted between the joint surfaces, and wherein the joint surface is at least one of meniscal surface, cartilage and subchondral bone.

15. The implant of claim 1, wherein the implant is expandable to a size sufficient to engage at least one joint surface when implanted between the joint surfaces, and wherein the joint surface is prepared prior to injection by at least one of meniscal removal, aperture creation, and abrasion.

16. The implant of claim 1, wherein the implant is expandable by the injection of material selected from the group consisting of: polymer, metal, gases, and crystal free metals.

17. The implant of claim 1, wherein the implant further incorporates an anchoring device.

18. The implant of claim 1, wherein the body further includes a wall that defines the cavity, the first exterior surface portion, and the second exterior surface portion of the body, wherein the wall has a variable thickness.

19. The implant of claim 1, wherein the body further includes a wall that defines the cavity and an exterior surface portion of the body, wherein the wall has a variable thickness.

20. The implant of claim 13 wherein the engaging of said perimeter assists in attaching or affixing the device to a surface.

21. A hollow device for forming an articular repair system in situ, the device having an aperture for injecting material into the device and a lumen coupled to the device to receive the material and form said articular repair system to treat a facet joint, uncovertebral joint or costovertebral joint in the spine, wherein the hollow device includes a first wall section and a second wall section formed from non-common materials so as to impart a varying expansion resulting in a desired shape of the device in an inflated state, and wherein the first wall section includes an exterior surface portion that substantially matches an articular surface portion.

22. An articular repair system formed in situ consisting of an injectable self-hardening material formed using a device as claimed in claim 21.

23. The device of claim 21, wherein said hollow device is bioresorbable.

24. A method of forming a customizable implant configured for placement between joint surfaces, the method comprising:
providing a first hollow device having walls with a variable wall thickness that imparts a varying expansion resulting in a desired shape of the device in an inflated state and having an exterior surface portion that substantially matches a corresponding surface portion of the joint;
inserting the first hollow device into a target joint; and
injecting material into the first hollow device to achieve the inflated state and the desired shape so as to form an implant to treat a facet joint, uncovertebral joint or costovertebral joint in the spine, wherein the exterior surface portion of the device engages the corresponding surface portion of the joint when the device is in the inflated state.

25. The method according to claim 24, further including the step of anchoring the implant to at least one of an articular surface, underlying bone, and adjacent bone.

26. The method according to claim 24, further including the step of removing surface irregularities in the target joint.

27. The method according to claim 26, wherein the surface irregularity is a bone spur.

28. The method according to claim 24, wherein the implant substantially conforms to a surface of the joint.

29. A method of forming a customizable implant configured for placement between joint surfaces, the method comprising:
providing a first hollow device having a first wall section and a second wall section formed from non-common materials so as to impart a varying expansion resulting in a desired shape of the device in an inflated state and having an exterior surface portion that substantially matches a corresponding surface portion of the joint;
inserting a first hollow device into a target joint; and
injecting material into the first hollow device to achieve the inflated state and the corresponding desired shape so as to form an implant to treat a facet joint, uncovertebral joint or costovertebral joint in the spine, wherein the exterior surface portion of the device engages the corresponding surface portion of the joint when the device is in the inflated state.

30. The method according to claim 29, further including the step of anchoring the implant to at least one of an articular surface, underlying bone, and adjacent bone.

31. The method according to claim 29, further including the step of removing surface irregularities in the target joint.

32. The method according to claim 31, wherein the surface irregularity is a bone spur.

33. The method according to claim 29, wherein the implant substantially conforms to a surface in the joint.

34. A method of forming a customizable implant configured for placement between joint surfaces, the method comprising:
providing a first hollow device having a varying expansion resulting in a desired shape of the device in an inflated state and having an exterior surface portion that substantially matches a corresponding surface portion of the joint;
inserting the first hollow device into a target joint;
injecting material into the first hollow devices to achieve the inflated state and the corresponding desired shape so as to form an implant to treat a facet joint, uncovertebral joint or costovertebral joint in the spine; and
anchoring the implant at least in part by engaging the exterior surface portion with the corresponding surface portion of the joint.

35. The method according to claim 34, further including the step of removing surface irregularities in the target joint.

36. The method according to claim 35, wherein the surface irregularity is a bone spur.

37. The method according to claim 34, wherein the implant substantially conforms to a surface in the joint.

38. The method of claim 34, wherein said anchoring is achieved by the implant substantially conforming in shape to at least one surface of a joint.

39. The method of claim 34, wherein said anchoring is achieved by the implant substantially conforming to the perimeter of a joint.

40. The method of claim 34, wherein said anchoring is achieved by the implant substantially conforming to a bone surface.

41. The method of claim 34, wherein said anchoring is achieved by the implant substantially conforming to a cartilage surface.

* * * * *